US010856850B2

(12) United States Patent
Ishida et al.

(10) Patent No.: US 10,856,850 B2
(45) Date of Patent: Dec. 8, 2020

(54) INFORMATION PROCESSING APPARATUS, METHOD, AND PROGRAM FOR MATCHING TARGET OBJECT POSITION BETWEEN THE PRONE AND SUPINE POSITIONS OBTAINED BY MRI AND ULTRASOUND

(71) Applicant: CANON KABUSHIKI KAISHA, Tokyo (JP)

(72) Inventors: Takuya Ishida, Tokyo (JP); Takaaki Endo, Urayasu (JP); Ryo Ishikawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1381 days.

(21) Appl. No.: 14/593,931

(22) Filed: Jan. 9, 2015

(65) Prior Publication Data

US 2015/0196282 A1   Jul. 16, 2015

(30) Foreign Application Priority Data

Jan. 10, 2014   (JP) .................................. 2014-003647

(51) Int. Cl.
*A61B 8/08*   (2006.01)
*A61B 8/00*   (2006.01)
(Continued)

(52) U.S. Cl.
CPC .......... *A61B 8/5261* (2013.01); *A61B 8/0825* (2013.01); *A61B 8/4245* (2013.01);
(Continued)

(58) Field of Classification Search
CPC ..... A61B 8/5261; A61B 5/055; A61B 8/0825; G06T 2207/10088; G06T 2207/10132; G06T 2207/30068
See application file for complete search history.

(56) References Cited

U.S. PATENT DOCUMENTS 5,579,360 A  * 11/1996 Abdel-Mottaleb .......................... A61B 6/4216
378/37
6,075,879 A  *  6/2000 Roehrig ................ G06F 19/321
382/132

(Continued)

FOREIGN PATENT DOCUMENTS

JP   2011-239974 A   12/2011

OTHER PUBLICATIONS

Song et al (Predicting Tumor Location from Prone to Supine Breast MRI Using a Simulation of Breast Deformation) 2013 IEEE International Conference on Granular Computing (GrC).*

(Continued)

*Primary Examiner* — Serkan Akar
(74) *Attorney, Agent, or Firm* — Canon U.S.A., Inc. I.P. Division

(57) ABSTRACT

An information processing apparatus includes acquisition units, calculation units, and a matching unit. The acquisition units acquire a position of a first reference point as a reference point, and a position of a first surface point as a point, on a surface of a target object in a first body posture. The acquisition units acquire a position of a second reference point as the reference point, and a position of a second surface point, on the surface of the target object in a second body posture. A distance between the first reference point position and the first surface point position is calculated as a first distance. A distance between the second reference point position and the second surface point position is calculated as a second distance. The matching unit matches the first and second surface points based on a relationship between the first and second distances.

11 Claims, 10 Drawing Sheets

(51) Int. Cl.
*A61B 5/055* (2006.01)
*G06T 7/35* (2017.01)
*G06T 7/33* (2017.01)

(52) U.S. Cl.
CPC ............ *A61B 8/4416* (2013.01); *G06T 7/344* (2017.01); *G06T 7/35* (2017.01); *A61B 5/055* (2013.01); *A61B 2576/00* (2013.01); *G06T 2200/04* (2013.01); *G06T 2207/10088* (2013.01); *G06T 2207/10132* (2013.01); *G06T 2207/20076* (2013.01); *G06T 2207/30068* (2013.01)

(56) References Cited

U.S. PATENT DOCUMENTS

| | | | |
|---|---|---|---|
| 2006/0251301 A1* | 11/2006 | McNamara, Jr. | A61B 6/0435 382/128 |
| 2009/0067694 A1* | 3/2009 | Shinagawa | G06T 7/0012 382/128 |
| 2011/0013819 A1* | 1/2011 | Raundahl | G06K 9/527 382/132 |
| 2012/0157819 A1* | 6/2012 | Jerebko | A61B 6/502 600/407 |
| 2012/0253173 A1* | 10/2012 | Endo | G06T 11/008 600/411 |

OTHER PUBLICATIONS

2012 Carbonaro et al (Contrast enhanced breast MRI: Spatial displacement from prone to supine patient's position. Preliminary results; European Journal of Radiology 81 (2012) e771-e774).*

Hu, A Statistical Motion Model Based on Biomechanical Simulations for Data Fusion during Image-Guided Prostate Interventions, book MICCAI 2008, pp. 737-744, 200, Part I, LNCS5241, publisher: Springer, Berlin Heidelberg, Germany.

* cited by examiner

INFORMATION PROCESSING APPARATUS, METHOD, AND PROGRAM FOR MATCHING TARGET OBJECT POSITION BETWEEN THE PRONE AND SUPINE POSITIONS OBTAINED BY MRI AND ULTRASOUND

BACKGROUND OF THE INVENTION

Field of the Invention

The present invention relates to an information processing apparatus, an information processing method, and a program, in particular to those that are favorably used for matching positions of a target object in different body postures.

Description of the Related Art

In the medical field, physicians make diagnosis by using medical images of a single subject captured by a plurality of modalities (medical image collection apparatuses) and medical images of a single subject captured at different dates and times. To use a plurality of types of medical images of a single subject to make diagnosis, it is important to match (identify) portions such as a lesion of interest (i.e., a portion of interest,) with each other in the different medical images. Thus, a physician, viewing an image of a lesion of interest indicated in one of the medical images, searches for a region corresponding to the lesion (i.e., a corresponding region, a corresponding lesion) in the other medical image based on similarity in the shape of the lesion or appearance of peripheral portions.

For example, in breast oncology departments, the diagnosis is made in the following manner in some cases. When a magnetic resonance imaging (MRI) image of a breast captured from a subject in a prone posture indicates a lesion, a corresponding lesion is searched (identified) in an ultrasonic cross-sectional image obtained by ultrasonography performed on the subject in a supine posture. However, the breast as an object is soft and thus largely changes its shape according to inspection positions. Thus, there is a problem in that the position and the appearance of the lesion largely differ between the MRI image and the ultrasonic cross-sectional image.

In view of the problem, Japanese Patent Application Laid-Open No. 2011-239974 discusses a technique of performing deformation processing on an MRI image to generate an MRI image matching with the shape of the subject at the time of ultrasonography.

However, when the deformation is estimated, a body surface point in the MRI image which does not match with a body surface point obtained in the ultrasonography, might be positioned close to the body surface point obtained at the time of ultrasonography. Thus, there is a problem in that the deformation might not be properly estimated.

SUMMARY OF THE INVENTION

The present invention is directed to accurately matching body surface points of the same subject in different body postures. For example, In an information processing apparatus, when matching a body surface point $qj$ of a subject in a supine posture and a vertex $pk$ of a mesh (a body surface point of the subject in a prone posture) is performed, candidates of corresponding points are narrowed down based on a relationship (ratio) between a geodesic distance $gk$ from a nipple to the vertex of the mesh and a direct distance $fj$ from the nipple to the body surface point $qj$ of the subject in the supine posture.

According to an aspect of the present invention, an information processing apparatus includes a first acquisition unit configured to acquire a position of a first reference point as a reference point on a surface of a target object in a first body posture, a second acquisition unit configured to acquire a position of a first surface point as a point on the surface of the target object in the first body posture, a third acquisition unit configured to acquire a position of a second reference point as the reference point on the surface of the target object in a second body posture different from the first body posture, a fourth acquisition unit configured to acquire a position of a second surface point as a point on the surface of the target object in the second body posture, a first calculation unit configured to calculate a first distance as a distance between the position of the first reference point and the position of the first surface point, a second calculation unit configured to calculate a second distance as a distance between the position of the second reference point and the position of the second surface point, and a matching unit configured to match the first surface point and the second surface point based on a relationship between the first distance and the second distance.

Further features of the present invention will become apparent from the following description of exemplary embodiments with reference to the attached drawings.

DESCRIPTION OF THE EMBODIMENTS

Figure 1:
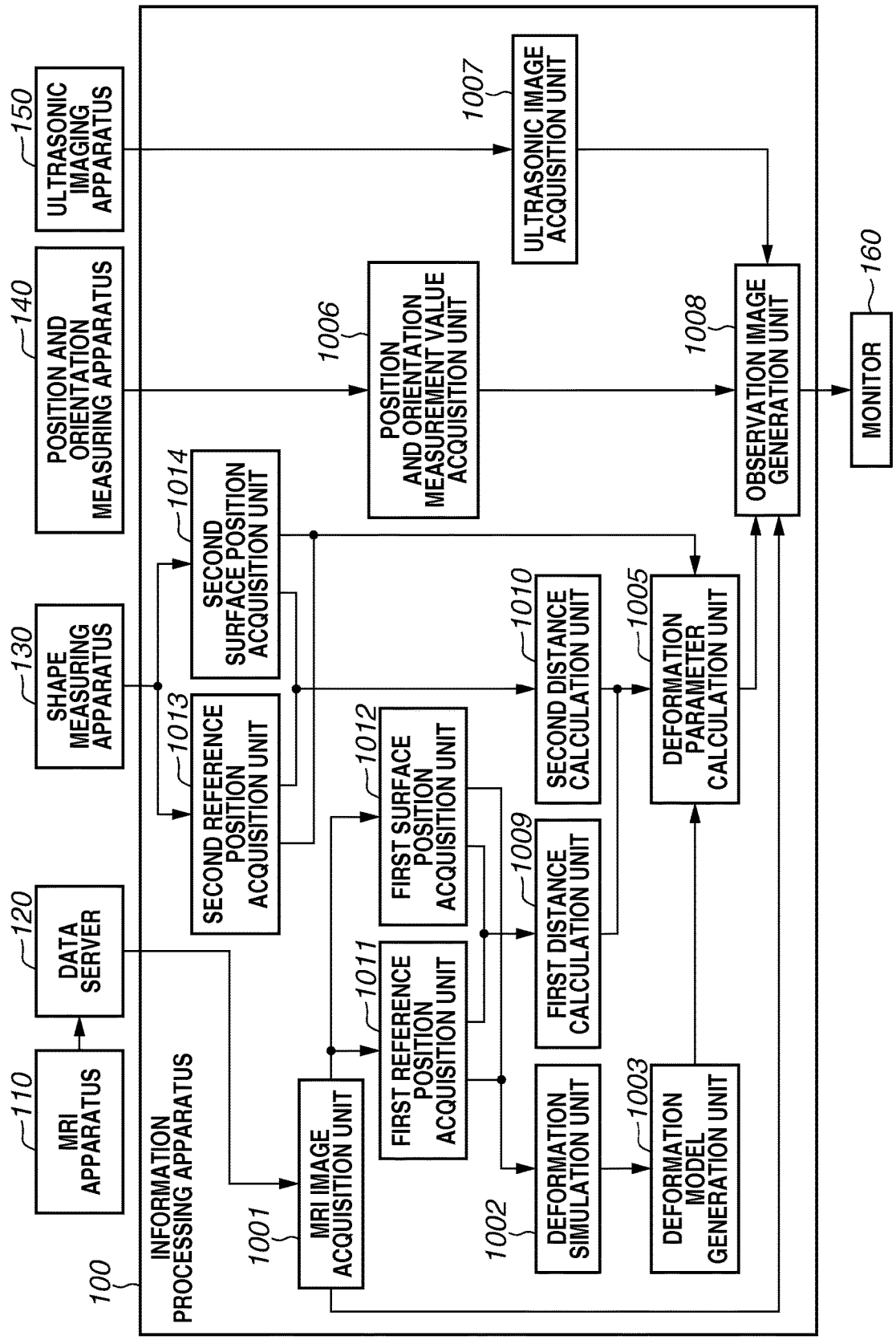
FIG. 1 is a diagram illustrating a first example of a configuration of a diagnostic system.

Exemplary embodiments of the present invention will be described by referring to the drawings.

A first exemplary embodiment will be described.

FIG. 1 is a diagram illustrating an example of a configuration of a diagnostic system. Specifically, FIG. 1 illustrates an example of a functional configuration of an information processing apparatus 100.

The information processing apparatus 100 performs deformation processing on an MRI image obtained by capturing a breast image of a subject in a prone posture, and thus generates an MRI image matching with a shape of an object (shape of the breast of the subject in a supine posture) at the time of ultrasonography. To that end, the information processing apparatus 100 acquires a body surface point group (positions on the body surface) and a reference point (nipple position) from the MRI image (the shape of the breast of the subject in the prone posture). The information processing apparatus 100 further acquires the body surface point group and the reference point (nipple position) from an ultrasonic image (the shape of the breast in the supine posture). The information processing apparatus 100 calculates a geodesic distance (shortest distance measured along the body surface) from the nipple to the body surface point group in the case of the prone posture. In the case of the supine posture, the information processing apparatus 100 calculates a direct distance (Euclidian distance) from the nipple to the body surface point group. The information processing apparatus 100 matches the body surface point of the MRI image with the body surface point of the ultrasonic image, based on the geodesic distance and the direct distance thus calculated. The information processing apparatus 100 performs deformation estimation of the MRI image based on the matching between the body surface points. Thus, in the present exemplary embodiment, as an example, the object (the breast of the subject) is a target object, the prone posture is a first position, and the supine posture is a second position.

In a case according to the present exemplary embodiment, the MRI image is used as an example of a medical image (three dimensional image data representing three dimensional information of the inside of the subject). However, the medical image is not limited to the MRI image, and may also be an X ray computed tomography (CT) image, a positron emission tomogram (PET) image, or the like.

In FIG. 1, the information processing apparatus 100 includes an MRI image acquisition unit 1001, a deformation simulation unit 1002, a deformation model generation unit 1003, a deformation parameter calculation unit 1005, a position and orientation measurement value acquisition unit 1006, and an ultrasonic image acquisition unit 1007. The information processing apparatus 100 further includes an observation image generation unit 1008, a first distance calculation unit 1009, a second distance calculation unit 1010, a first reference position acquisition unit 1011, a first surface position acquisition unit 1012, a second reference position acquisition unit 1013, and a second surface position acquisition unit 1014. The information processing apparatus 100 is connected to a data server 120, a shape measuring apparatus 130, a position and orientation measuring apparatus 140, and an ultrasonic imaging apparatus 150.

An MRI apparatus 110 is an apparatus that captures an MRI image by acquiring information on a three dimensional area within the subject (a human body) by the nuclear magnetic resonance method. The MRI apparatus 110 is connected to the data server 120, and, for example, transmits the MRI image, obtained by capturing the breast image of the subject in the prone posture, to the data server 120.

The data server 120 is an apparatus that stores the MRI image and the like captured by the MRI apparatus 110.

The ultrasonic imaging apparatus 150 captures an ultrasonic image of the inside of the subject with an unillustrated ultrasonic probe that is brought in contact with the subject and transmits and receives ultrasonic waves. In the present exemplary embodiment, the ultrasonic imaging apparatus 150 captures a two dimensional B mode ultrasonic image of a cross-sectional area of a breast of the subject in the supine posture.

The position and orientation measuring apparatus 140 is an apparatus that measures a position and an orientation of the ultrasonic probe in a three dimensional space. The position and orientation measuring apparatus 140 is, for example, a six-degrees-of-freedom measurement apparatus of a magnetic type or an optical type attached to the ultrasonic probe.

The shape measuring apparatus 130 is an apparatus that measures the nipple position and the body surface shape of the subject. The shape measuring apparatus 130 is formed of a conventionally known member such as a stylus (a pen-shaped device having a function to measure the position at a distal end portion) that is brought into contact with a body surface position of the subject and measures the shape, for example. In the present exemplary embodiment, the shape measuring apparatus 130 is disposed at a position adjacent to the ultrasonic imaging apparatus 150 and the position and orientation measuring apparatus 140. The shape measuring apparatus 130 measures the nipple position and the positions of several body surface points, as information on the shape of the subject (the shape of the subject in the supine posture) at the time of performing ultrasonography.

Next, each component of the information processing apparatus 100 will be described.

The MRI image acquisition unit 1001 acquires the MRI image (the image of the breast of the subject in the prone posture) captured by the MRI apparatus 110 through the data server 120.

The first reference position acquisition unit 1011 performs image analysis processing on the MRI image acquired by the MRI image acquisition unit 1001 to perform first acquisition processing to acquire the nipple position as a first reference position (first reference point).

The first surface position acquisition unit 1012 performs image analysis processing on the MRI image acquired by the MRI image acquisition unit 1001 to perform second acquisition processing to acquire positions of the body surface point group of the breast as first body surface positions (first body surface points). The first surface position acquisition unit 1012 calculates a breast area surrounded by a body surface and a greater pectoral muscle surface, as information indicating the shape of the subject.

The deformation simulation unit 1002 calculates through a simulation the deformation of the shape of the subject (breast of the subject) occurring when the subject changes to the supine posture. The simulation is based on the nipple position acquired by the first reference position acquisition unit 1011 and the breast area acquired by the first surface position acquisition unit 1012. The deformation simulation unit 1002 calculates a plurality of deformations of the subject (the breast of the subject) under different conditions through a processing method described later.

The deformation model generation unit 1003 generates a deformation model expressing the deformations of the subject with a plurality of parameter sets, based on the result of the plurality of deformations of the subject calculated by the deformation simulation unit 1002. In the present exemplary embodiment, the plurality of parameter sets is referred to as a parameter vector as appropriate.

The first distance calculation unit 1009 performs first calculation processing. In the first calculation processing, the geodesic distance from the nipple to each body surface point of the subject in the prone posture is calculated. The calculation is based on the nipple position acquired by the first reference position acquisition unit 1011 and positions of the body surface point group acquired by the first surface position acquisition unit 1012.

The second reference position acquisition unit 1013 performs third acquisition processing of acquiring the nipple position of the subject at the time of ultrasonography measured by the shape measuring apparatus 130, as a second reference position (second reference point).

The second surface position acquisition unit 1014 performs fourth acquisition processing of acquiring positions of several body surface points of the subject in the supine posture at the time of ultrasonography, as second surface positions (second body surface points).

The second distance calculation unit 1010 performs second calculation processing. In the second calculation processing, the direct distance from the nipple to each body surface point of the subject in the supine posture is calculated. The calculation is based on the nipple position acquired by the second reference position acquisition unit 1013 and the positions of the several body surface points acquired by the second surface position acquisition unit 1014.

The deformation parameter calculation unit 1005 (matching unit) acquires the deformation model generated by the deformation model generation unit 1003. The deformation parameter calculation unit 1005 acquires the geodesic distance from the nipple to the body surface point of the subject in the prone posture calculated by the first distance calculation unit 1009. The deformation parameter calculation unit 1005 further acquires the direct distance from the nipple to the body surface of the subject in the supine posture calculated by the second distance calculation unit 1010. The deformation parameter calculation unit 1005 matches the body surface point of the subject in the prone posture with the body surface point of the subject in the supine posture, based on the deformation model, the geodesic distance from the nipple to the body surface of the subject in the prone posture, and the direct distance from the nipple to the body surface of the subject in the supine posture. The deformation parameter calculation unit 1005 calculates the parameter vector with a minimum approximation error in the approximation of the deformation using the deformation model, based on the sum of the distances between matching ones of the body surface points of the subject in the prone posture and the body surface points of the subject in the supine posture.

The position and orientation measurement value acquisition unit 1006 acquires measurement values of the position and the orientation of the ultrasonic probe measured by the position and orientation measuring apparatus 140.

The ultrasonic image acquisition unit 1007 acquires an ultrasonic image of the inside of the subject, acquired by the ultrasonic imaging apparatus 150.

The observation image acquisition unit 1008 performs deformation processing on the MRI image obtained by capturing an image of the breast of the subject in the prone posture, based on the parameter vector calculated by the deformation parameter calculation unit 1005. Thus, the observation image acquisition unit 1008 generates an MRI image (deformed MRI image) of the breast of the subject in the supine posture. The observation image acquisition unit 1008 clips and thus generates an image (corresponding cross-sectional image) corresponding to the ultrasonic image from the deformed MRI image, based on the measurement values of the position and the orientation of the ultrasonic prove acquired by the position and orientation measurement value acquisition unit. The observation image acquisition unit 1008 generates an observation image by superimposing the corresponding cross-sectional image thus generated on the ultrasonic image acquired by the ultrasonic image acquisition unit 1007.

A monitor 160 displays the observation image generated by the observation image acquisition unit 1008.

Figure 2:
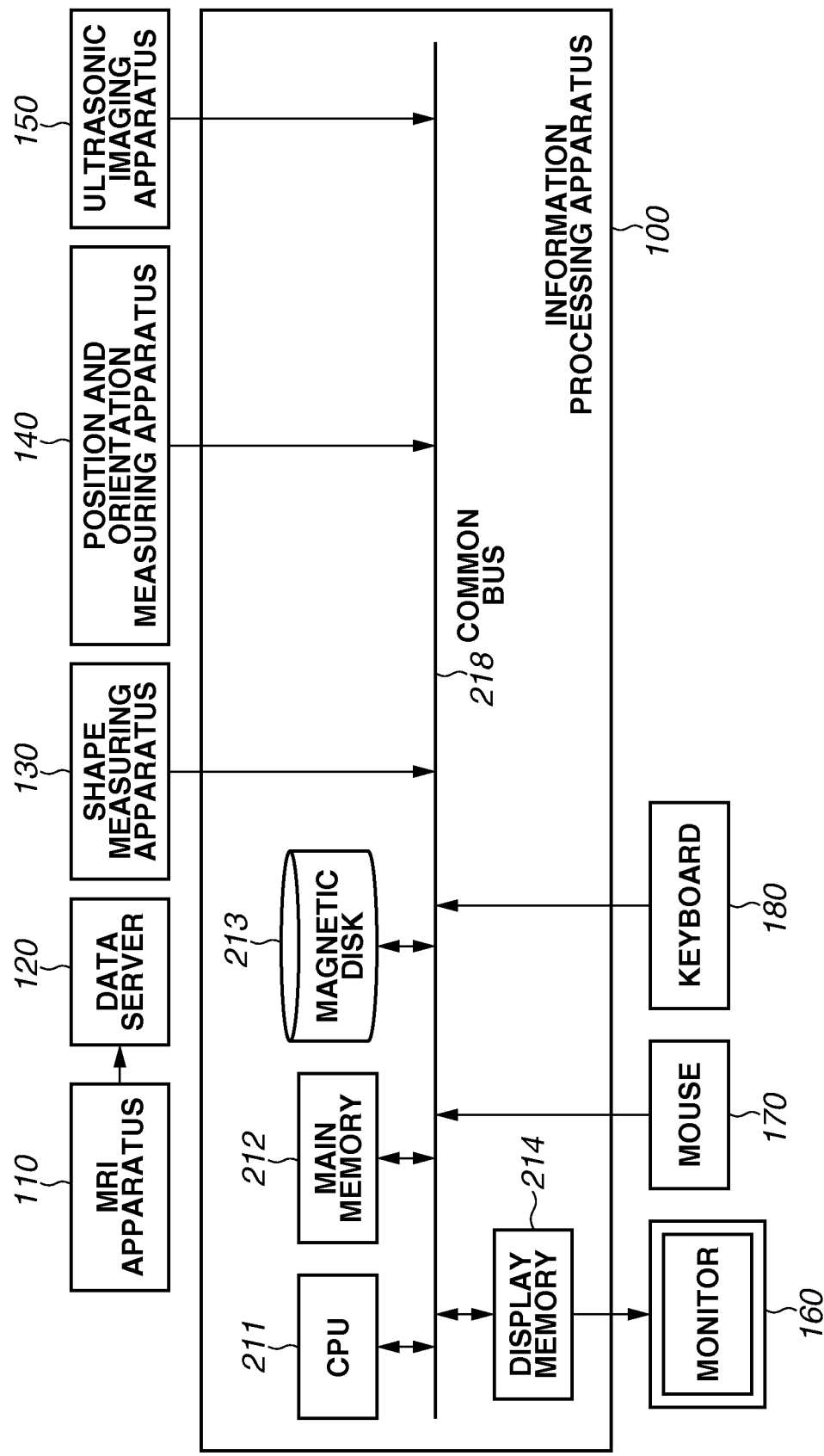
FIG. 2 is a diagram illustrating a hardware configuration of the diagnostic system.

FIG. 2 is a diagram illustrating an example of a hardware configuration of the diagnostic system. In particular, an example of a hardware configuration of the information processing apparatus 100 is illustrated in FIG. 2.

The diagnostic system includes the information processing apparatus 100, the MRI apparatus 110, the data server 120, the shape measuring apparatus 130, the position and orientation measuring apparatus 140, the ultrasonic imaging apparatus 150, the monitor 160, a mouse 170, and a keyboard 180.

The information processing apparatus 100 can be constituted by a personal computer (PC) and the like, for example. The information processing apparatus 100 includes a central processing unit (CPU) 211, a main memory 212, a magnetic disk 213, and a display memory 214.

The CPU 211 mainly controls an operation of each component of the information processing apparatus 100. The main memory 212 stores a control program executed by the CPU 211 and provides a work area for the CPU 211 to execute the program. The magnetic disk 213 stores an operating system (OS), a device drive for a peripheral device, various types of application software including a program for executing processing described later, and the like. The display memory 214 temporarily stores display data for the monitor 160. The monitor 160, which is a cathode ray tube (CRT) monitor, a liquid crystal monitor, or the like for example, displays an image based on the data from the display memory 214. The mouse 170 and the keyboard 180 are used by the user in inputting the pointing and characters and commands. The components are communicably coupled to each other through a common bus 218.

Figure 3:
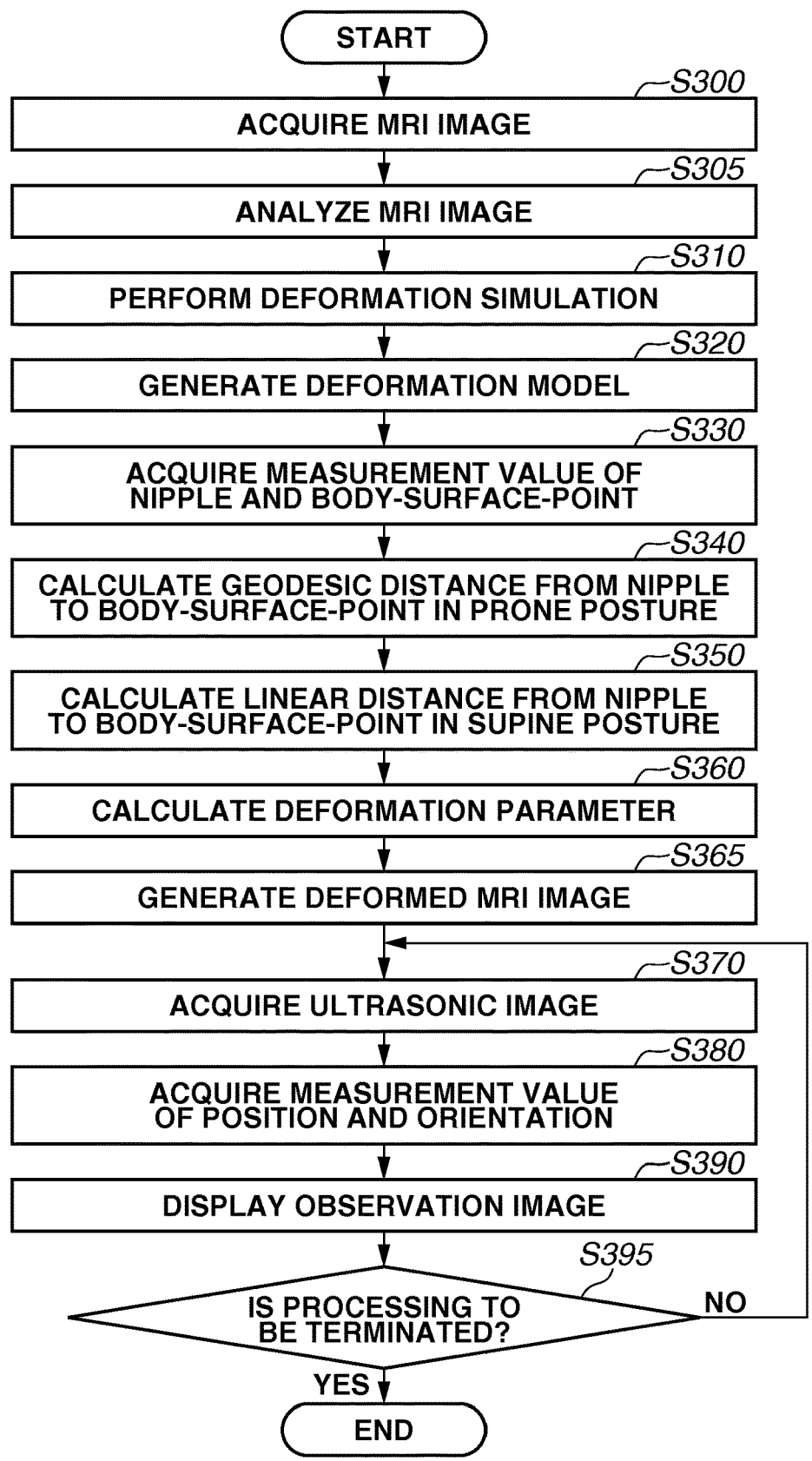
FIG. 3 is a flowchart illustrating a first example of the entire processing performed by an information processing apparatus.

Next, an example of the entire processing performed by the information processing apparatus 100 will be described in detail by referring to a flowchart in FIG. 3. In the present exemplary embodiment, the processing in the flowchart in FIG. 3 is realized when the CPU 211 executes a program, stored in the main memory 212, for implementing a function of each component. The result of each operation performed by the information processing apparatus 100 described later is stored and thus recorded in the main memory 212.

(Step S300)

First of all, in step S300, the MRI image acquisition unit 1001 acquires the three dimensional MRI image, captured by the MRI apparatus 110, from the data server 120. Here, the MRI image acquisition unit 1001 acquires the three dimensional MRI image, obtained by capturing an image of the subject breast in the prone posture, from the data server 120.

(Step S305)

In step S305, the first reference position acquisition unit 1011 performs the image analysis processing on the MRI image obtained in step S300 to acquire the nipple position as the first reference position and the positions of the dense body surface point group as the first surface positions. Furthermore, the first reference position acquisition unit 1011 calculates the breast area surrounded by the body surface and the greater pectoral muscle surface, as information indicating the shape of the subject.

(Step S310)

In step S310, the deformation simulation unit 1002 calculates the deformation of the breast of the subject occurring when the subject changes the position from the prone posture to the supine posture as the ultrasonic inspection position, through physical simulation. The processing can be executed by a conventionally known method such as a finite element method for example. An example of the processing method will be described.

The deformation simulation unit 1002 first obtains the breast area and the nipple position acquired from the MRI image in step S305, and sets the area as a target area of the physical simulation.

Next, the deformation simulation unit 1002 divides the target area of the physical simulation thus set into meshes formed by a plurality of vertices. An appropriate conventionally known method can be used to automatically execute the above-described processing. In the present exemplary embodiment, "$p_k$" represents a vertex of each of the meshes obtained by dividing the region, "$s_k$" represents coordinates of the position of the vertex, and a vector $s=(x1, y1, z1, \ldots, xk, yk, zk, \ldots, xN, yN, zN)^t$ represents the position coordinates of vertices that form meshes obtained by dividing the region, in which "k" is a suffix allocated to each vertex of the mesh and satisfies the relationship $1 \le k \le N$. Further, "N" represents the total number of the vertices. In the present exemplary embodiment, it is presumed that Q pieces of vertices are positioned on the body surface of the subject ($Q \le N$). Further, it is presumed that the first element to the ($3 \times Q$)th element of the vector s store position coordinates of the Q pieces of vertices positioned on the body surface of the subject.

The deformation simulation unit 1002 searches for the vertex of the mesh positioned at the body surface of the subject closest to the acquired nipple position, and sets the vertex as a nipple node. The values of respective elements forming the vector s are the position coordinates defined in the MRI image coordinate system.

Subsequently, the deformation simulation unit 1002 sets simulation conditions (including mechanical properties of a material that constitutes a simulation target area and a variation in the direction of gravity that causes a deformation), and generates a stiffness matrix based on the simulation conditions. For example, assuming that the breast is a linear elastic body, the simulation conditions to be set by the deformation simulation unit 1002 can include Young's modulus and Poisson's ratio as the mechanical properties of the material. However, in the present exemplary embodiment, it is presumed that the Young's modulus and the Poisson's ratio are unknown. More specifically, the deformation simulation unit 1002 performs the following processing for each of a plurality of different conditions, when a plurality of combinations of the Young's modulus and the Poisson's ratio is made. For example, the deformation simulation unit 1002 selects one of 500 [Pa], 1000 [Pa], 2000 [Pa] and 4000 [Pa] as the Young's modulus and selects one of 0.3, 0.4, and 0.49 as the Poisson's ratio to obtain twelve combinations of the Young's modulus and the Poisson's ratio (i.e., simulation conditions). The deformation simulation unit 1002 performs the following processing under each of the simulation conditions.

Subsequently, the deformation simulation unit 1002 sets a load to be applied to each vertex of the mesh that forms the target area of the physical simulation. In the present exemplary embodiment, the processing apparatus simulates a deformation when the subject changes the position from the prone posture to the supine posture. Thus, the deformation simulation unit 1002 calculates, as a setting value, a load caused by a difference in the direction of gravity Subsequently, the deformation simulation unit 1002 calculates a displacement of each vertex that forms the mesh (i.e., a divided part of the target area of the physical simulation) based on the stiffness matrix and the load calculated in the above-described manner. The above-described processing is equivalent to calculating a deformation state of the subject. In the present exemplary embodiment, the deformation state is numerical information representing the position of each vertex of a deformed mesh. In the present exemplary embodiment, the deformation state of the subject calculated for each of the twelve different simulation conditions is expressed using a vector $di=(x1_i, y1_i, z1_i, \ldots, xN_i, yN_i, zN_i)^t$ that represents the position coordinates $dk_i$ of vertices $p_k$ after the deformation, in which "i" is a suffix allocated to each of the simulation conditions and is an integer equal to or larger than 1 and equal to or smaller than 12 ($1 \le i \le 12$). Further, the value of each of the elements of the vector di is the position coordinates defined in the MRI image coordinate system (a position coordinate of the vertex of each mesh).

Subsequently, the deformation simulation unit 1002 moves the position of the vertex of each mesh without changing the relative relationship among the meshes, such that the nipple node is positioned at the origin, for each deformed state of the subject calculated under each simulation condition. Specifically, the deformation simulation unit 1002 calculates an amount of movement of the nipple node up to the origin in the deformed state of the subject, under each simulation condition, and translating the vertices of the other meshes by the amount of movement thus calculated.

According to the above-described example, the finite element method is employed as the simulation method to obtain the deformation of the breast occurring when the subject changes its body posture to the supine posture as the inspection position from the prone posture. However, the simulation method according to the present invention is not limited to the above-described example. Any other appropriate method (e.g., a difference method or a particle method) is employable to simulate the deformation of the breast occurring when the subject changes the position from the prone posture to the supine posture as the inspection position.

(Step S320)

In step S320, the deformation model generation unit 1003 generates a deformation model that parametrically expresses the deformation based on the simulation result $d_i$ (result of the simulation of the deformation of the subject) calculated in step S310. For example, an example deformation model generation method is discussed by Yipeng Hu, et al., "A Statistical motion model based on biomechanical simulations for data fusion during image-guided prostate interventions," MICCAI 2008, Part I, LNCS 5241, pp. 737 and 744, 2008.

According to the method discussed by Yipeng Hu, et al., a normalized vector $\tilde{d}_i$ is generated by dividing each simulation result $d_i$ by an average vector $d_{ave}$ of the simulation results. Principal component analysis is performed on the normalized vector $\tilde{d}_i$, and M pieces of principal component vectors ranging from the first principal component vector $e_1$ to the Mth principal component vector $e_M$ are obtained. The deformation model can be generated by the deformation model generation unit 1003 in this step S320 based on the calculation of the information on the average vector $d_{ave}$ and the principal component vector $e_i$. In the present exemplary embodiment, the above-described information is referred to as the deformation model.

The deformation model will be described below. Various deformation states "r" including the simulation result di can be generated by calculating a linear sum obtained by weighting the principal component vectors $e_i$ calculated through the above-described processing with parameters $c_1$ to $c_M$ whose number is equal to the total number of the principal component vectors $e_i$, as expressed in the following formula (1).

$$r = d_{ave} + \sum_{i=1}^{M} c_i e_i \quad (1)$$

The formula (1) can be rewritten into a combined matrix and vector format, as expressed with the following formula (2).

$$r = d_{ave} + Ec \quad (2)$$

In the above-described formula (4), "E" is a matrix including the principal component vectors $e_1$ to $e_M$ arranged in the horizontal direction and "c" represents a vector including the parameters $c_1$ to $c_M$ arranged in the vertical direction. In the present exemplary embodiment, the vector "c" is referred to as the parameter vector. The deformation model generated in step S320 expresses various deformation states through the calculation process of formula (2), by changing elements of the parameter vector c in various manners. In the present exemplary embodiment, "$r_k$" represents position coordinates of respective vertices $p_k$ forming meshes in a deformation state expressed by the deformation model. The position coordinates of respective vertices of meshes can be regarded as a function $r_k(c)$ that is variable depending on the parameter vector c.

(Step S330)

Referring back to FIG. 3, in step S330, the second reference position acquisition unit 1013 acquires the nipple position of the subject in the supine posture, measured by the shape measuring apparatus 130. The second surface position acquisition unit 1014 acquires positions of arbitrary several body surface points other than the nipple of the subject in the supine posture measured by the shape measuring apparatus 130. In the present exemplary embodiment, "$t_0$" represents the coordinates of the measured nipple position, "$q_j$" represents the jth body surface point, and "$t_j$" represents the position coordinate of the jth body surface point, under a condition $1 \leq j \leq L$, where "L" represents the number of measured points.

(Step S340)

In step S340, the first distance calculation unit 1009 calculates the geodesic distance from the nipple to each of the body surface points. The calculation is based on the positions of the dense body surface point group in the supine posture and the nipple position, acquired in step S305. The first distance calculation unit 1009 generates a geodesic distance map in which each of sets of coordinates representing the respective positions of the dense body surface point group holds a geodesic distance from the nipple to the position (each body surface point).

(Step S350)

In step S350, the second distance calculation unit 1010 calculates the direct distance $f_j$ from the nipple to each of the body surface points $q_j$ ($1 \leq j \leq L$) of the subject in the supine posture, acquired in step S330.

(Step S360)

Figure 4:
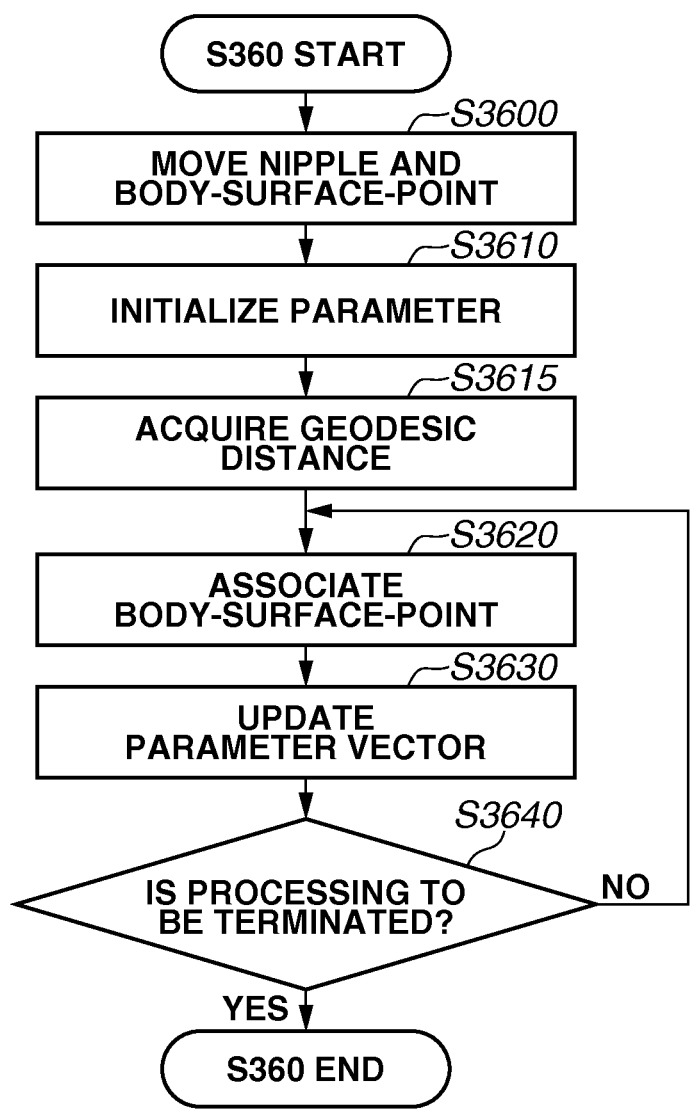
FIG. 4 is a flowchart illustrating an operation in step S360 in detail.

In step S360, the deformation parameter calculation unit 1005 calculates deformation parameters of the deformation model in which the deformation state expressed by the deformation model generated in step S320 substantially coincides with the measurement values of the body surface points of the subject obtained in step S330. A detail example of the processing in step S360 is described below by referring to a flowchart in FIG. 4.

(Step S3600)

In step S3600, the deformation parameter calculation unit 1005 moves the nipple position of the subject in the supine posture, acquired in step S330, to the origin. Then, the deformation parameter calculation unit 1005 causes the other body surface point group acquired in step S330 to make a translational motion, based on the amount of movement of the nipple position. In the processing described below, "tj" represents the position coordinate of the body surface point qj after the translation.

(Step S3610)

In step S3610, the deformation parameter calculation unit 1005 sets an initial value of the parameter vector c. For example, the initial value of the parameter vector c may be set by setting the most common simulation condition in advance, and obtaining a vector c representing the deformation shape based on the simulation condition. Alternatively, a zero vector may be set as the initial value of the parameter vector c. In the latter case, the initial deformation parameter is the average vector $d_{ave}$ of the simulation results $d_i$ according to formula (1).

(Step S3615)

In step S3615, the deformation parameter calculation unit 1005 acquires the geodesic distance from the nipple to each of the vertices $p_k$ ($1 \leq k \leq Q$) of the respective meshes generated in step S310, which is in the state before the deformation. Specifically, the coordinates of the body surface point closest to the position $s_k$ of the vertex $p_k$ of the mesh before the deformation are obtained. The deformation parameter calculation unit 1005 acquires the geodesic distance corresponding to the coordinates in the geodesic distance map generated in step S340, and sets the geodesic distance as a geodesic distance $g_k$ from the nipple to the vertex $p_k$ of the mesh in the state before deformation.

(Step S3620)

In step S3620, the deformation parameter calculation unit 1005 matches each of the body surface points $q_j$ ($1 \leq j \leq L$) with the vertex $p_k$ of the mesh. Here, the geodesic distance $g_k$ between the nipple and the vertex $p_k$ of the mesh and the direct distance $f_j$ from the nipple to the body surface point $q_j$ of the subject in the supine posture, calculated in step S350, are compared, and the candidates of matching point are narrowed down based on the relationship between the distances. In the present exemplary embodiment, only the vertex $p_k$ showing the ratio of the geodesic distance $g_k$ to the direct distance $f_j$ within a predetermined range (within a range defined by the lower limit value and the upper limit value) is set as the candidate of the matching point. The deformation parameter calculation unit 1005 selects the vertex $p_k$ with the position coordinate $r_k(c)$, which is obtained by the deformation based on the current parameter vector c and is closest to the position coordinate $t_j$ of the subject in the supine posture, from among the candidates of the matching points. The deformation parameter calculation unit 1005 selects the vertex $p_k$ thus selected as the corresponding point of the body surface point $q_j$ of the subject in the supine posture.

The range of the ratio of the geodesic distance $g_k$ to the direct distance $f_j$ is described further in detail. The vertex $p_k$ of the mesh as a candidate of a point (corresponding point) matching the body surface point $q_j$ of the subject in the supine posture satisfies the following formula (3).

$$\frac{1}{\varepsilon} < \frac{f_j}{g_k} < \varepsilon \qquad (3)$$

In the formula, "$\varepsilon$" is a positive constant related to a relaxation ratio of the restriction for narrowing down the candidates of the corresponding point. "$\varepsilon$" is set based on a ratio between stretching and shrinking on the body surface of the subject occurring when the subject changes the position from the prone posture to the supine posture, for example.

Formula (3) is described more in detail. The processing of narrowing down the candidates of the corresponding point is based on the knowledge that the skin of the breast is not stretched or shrunk by the deformation occurring when the body posture changes. Based on the knowledge, a geodesic distance $o_i$ from the nipple to the body surface point $q_j$ of the subject satisfies the following formula (4). In the present exemplary embodiment, the geodesic distance $o_i$ from the nipple to the body surface point $q_j$ of the subject in the supine posture is not calculated.

$$\frac{1}{\varepsilon} < \frac{o_i}{g_k} < \varepsilon \qquad (4)$$

The geodesic distance $o_i$ from the nipple to the body surface point $q_j$ of the subject in the supine posture is always longer than the direct distance $f_j$ from the nipple to the body surface point $q_j$. The relationship between the geodesic distance $o_i$ and the direct distance $f_j$ is expressed in the following formula (5).

$$o_i = f_j + \varepsilon_{ge} \qquad (5)$$

In the formula, "$\varepsilon_{ge}$" is a real positive number representing the difference between the geodesic distance and the direct distance. The inequality of formula (3), as well as formulae (4) and (5), holds true when "$\varepsilon_{ge}$" is 0 ($\varepsilon_{ge}=0$). In a case of the actual subject, the geodesic distance $o_i$ does not exactly match with the direct distance $f_j$, and "$\varepsilon_{ge}$" in Formula (5) is generally larger than 0. Thus, for example, $\varepsilon_{ge}=\alpha$ (positive constant value) may be set. In this case, the ratio of the geodesic distance $g_k$ to the direct distance $f_j$ is expressed in the following formula (6), based on formulae (4) and (5).

$$\frac{1}{\varepsilon} - \frac{\alpha}{g_k} < \frac{f_j}{g_k} < \varepsilon - \frac{\alpha}{g_k} \qquad (6)$$

The range of the ratio of the geodesic distance $g_k$ to the direct distance $f_j$ is wider on the lower end side and narrower on the upper end side in formula (6) than in formula (3). Thus, the range defined by the upper and lower end values of the ratio of the geodesic distance $g_k$ to the direct distance $f_j$ is shifted in a direction that the direct distance in the supine posture becomes shorter than the geodesic distance in the prone posture. In the example described above, "$\varepsilon_{ge}$" is not limited to a constant as in the example described above, and may be a function of the direct distance $f_j$ or the geodesic distance $g_k$. For example, "$\varepsilon_{ge}$" may be a linear function of the direct distance $f_j$ between the nipple and the body surface point of the subject in the supine posture, and the farther the position of the body surface point stays from the nipple, the smaller the range of the ratio of the body surface point to the candidate becomes by shifting in such a direction. Thus, the condition for narrowing down the candidates can be changed in accordance with the distance from the nipple.

Alternatively, "$\varepsilon_{ge}$" may be determined based on the prior knowledge about the body surface shape and the like. For example, a large "$\varepsilon_{ge}$" may be used when the body surface shape of the subject has a large curvature. Through the methods described above, the candidates of the corresponding point can be more accurately narrowed down in consideration of the difference between the geodesic distance $o_i$ from the nipple to the body surface point $q_j$ of the subject in the supine posture and the direct distance $f_j$ from the nipple to the body surface point $q_j$.

In the processing described above, the difference between the direct distance $f_j$ and the geodesic distance $g_k$ may be used instead of the ratio between the direct distance $f_j$ and the geodesic distance $g_k$.

The processing of narrowing down the candidates of the corresponding point in step S3620 is based on the knowledge that the geodesic distance from the nipple to each body surface point is maintained even when the breast is deformed by the position change (the skin is unlikely to be shrunk or stretched). The direct distance from the nipple to the body surface point is used instead of the geodesic distance in the case of the supine posture, because the dense body surface shape is difficult to measure at the time of ultrasonography. This is based on an idea that approximating the geodesic distance by the direct distance is effective as the constraint condition because the breast is deformed to a flat shape when the body posture changes to the supine posture. By changing the condition for narrowing down the candidates in accordance with the distance from the nipple, the candidates can be narrowed down while taking into account the difference between the geodesic distance and the direct distance from the nipple to the body surface point. Thus, the problem caused by using the direct distance instead of the geodesic distance can be alleviated.

(Step S3630)

In step S3630, the deformation parameter calculation unit 1005 performs processing of obtaining the parameter vector c (updating the parameter vector c) that minimizes a distance function $L_{dist}(c)$ defined by the following formula (7).

$$L_{dist}(c) = \frac{1}{L} \sum_{j=1}^{L} \|t_j - r_j(c)\|^2 \qquad (7)$$

In other words, deformation with the minimum sum of distances between the corresponding points obtained by the processing in step S3620 is estimated. In formula (7), "$r_j(c)$" represents coordinates $r_k(c)$ of the vertex $p_k$ of the mesh which matches with the body surface point $q_j$ of the subject in the supine posture. The above-described processing can be performed by solving a nonlinear optimization problem. For example, a conventionally known method (e.g., a steepest descent method or a quasi-Newton method) is usable.

(Step S3640)

In step S3640, the deformation parameter calculation unit 1005 determines whether the processing of calculating the parameter vector c is to be terminated. For example, the deformation parameter calculation unit 1005 determines to continue the processing when the residual of formula (7) is not smaller than a predetermined value, and determines to terminate the processing when the residual is smaller than the predetermined value. When the deformation parameter calculation unit 1005 determines to continue the processing, the processing proceeds to step S3620. Thus, the operation in step S3620 (matching each of the body surface points $q_j$ of the subject in the supine posture with the vertex $p_k$ of the mesh) and the operation in step S3630 (updating the parameter vector c) are executed again based on the updated parameter vector c.

The deformation parameter calculation processing in step S360 is performed as described above.

(Step S365)

In step S365, the observation image acquisition unit 1008 performs the deformation processing on the MRI image acquired in step S300 based on the deformation parameter calculated in step S360. Thus, the deformed MRI image having the shape matching the position of the subject at the time of ultrasonography is generated.

(Step S370)

In step S370, the ultrasonic image acquisition unit 1007 acquires the ultrasonic image (image of the breast of the subject in the supine posture) captured by the ultrasonic imaging apparatus 150.

(Step S380)

In step S380, the position and orientation measurement value acquisition unit 1006 acquires the measurement values related to the position and the orientation of the ultrasonic probe measured by the position and orientation measuring apparatus 140.

(Step S390)

In step S390, the observation image acquisition unit 1008 clips the image of the surface defined by the position of the orientation of the ultrasonic probe acquired in step S380 from the deformed MRI image generated in step S365. Thus, the cross-sectional image is generated. The observation image acquisition unit 1008 generates the observation image obtained by superimposing the cross-sectional image thus generated on the ultrasonic image acquired in step S370. The observation image is displayed on the monitor 160. The ultrasonic image and the cross-sectional image may be displayed side-by-side.

(Step S395)

In step S395, the information processing apparatus 100 terminates the processing or returns the processing to S370, based on the determination made by the user through an input operation on the mouse 170 or the keyboard 180.

The processing by the information processing apparatus 100 is performed as described above.

As described above, the information processing apparatus according to the present exemplary embodiment includes a first acquisition unit (the first reference position acquisition unit 1011) configured to acquire a position of a first reference point on a surface of a target object in a first body posture, a second acquisition unit (the first surface position acquisition unit 1012) configured to acquire a body posture of a first surface point on the surface of the target object in the first position, a third acquisition unit (the second distance calculation unit 1013) configured to acquire a body posture of a second reference point on the surface of the target object in a second body posture different from the first position, a fourth acquisition unit (the second surface position acquisition unit 1014) configured to acquire a position of a second surface point as a point on the surface of the target object in the second body posture, a first calculation unit (the first distance calculation unit 1009) configured to calculate a first distance as a distance between the position of the first reference point and the position of the first surface point, a second calculation unit (the second distance calculation unit 1010) configured to calculate a second distance between the position of the second reference point and the position of the second surface point, and a matching unit (the deformation parameter calculation unit 1005) configured to match the first surface point with the second surface point based on a relationship between the first distance and the second distance.

In other words the information processing apparatus includes an acquisition unit (the first reference position acquisition unit 1011 and the first surface position acquisition unit 1012) configured to acquire positions of a reference point and a surface point on a surface of a target object in the first body posture, an acquisition unit (the second distance calculation unit 1013 and the second surface position acquisition unit 1014) configured to acquire positions of a reference point and a surface point on the surface of the target object in the second body posture, and a matching unit (the deformation parameter calculation unit 1005) configured to match between the surface point in the first body posture and the surface point in the second body posture, based on a distance between the reference point and the surface point in the first body posture and a distance between the reference point and the surface point in the second body posture.

Thus, it is possible to provide a mechanism for deforming the MRI image, captured when the subject is in the prone posture, to match the shape in the supine posture with that in the prone posture so that the MRI image corresponding to the supine posture as the capturing position can be presented at the time of ultrasonography.

In the present exemplary embodiment in particular, when the matching the body surface point $q_j$ of the subject in the supine posture with the vertex $p_k$ of the mesh (the body surface point of the subject in the prone posture) is performed, the candidates of the corresponding points are narrowed down based on the relationship between the geodesic distance $g_k$ from the nipple to the vertex $p_k$, and the straight distance $f_j$ from the nipple to the body surface point $q_j$. Thus, erroneous matching can be prevented even when the vertex $p_k$ of the mesh, which is actually not the corresponding point, is positioned close to the body surface point $q_j$ of the subject in the supine posture due to an inappropriate estimation value of the current deformation. As a result, the deformation of the monitored portion such as the breast due to the change of the body posture of the subject can be more accurately estimated. As a consequence, the MRI image captured in the prone posture can be deformed to match the shape in the supine posture, so that the MRI image matching the supine posture for capturing the ultrasonic image can be presented to an operator.

Modified Example 1

In the operation of step S3620 in the present exemplary embodiment, the direct distance from the nipple to the body surface point $q_j$ of the subject in the supine posture is used as the second distance serving as information for narrowing down the candidates of the corresponding point. However, the second distance is not limited to the direct distance. For example, a simplified shape including a plurality of triangular patches may be obtained by using positions of a plurality of body surface points of the subject in the supine posture. Thus, the geodesic distance from the geodesic distance may be obtained based on the simplified shape. Alternatively, a low order surface model expressed by an implicit polynomial and the like, may be applied to the positions of a plurality of body surface points of the subject in the supine posture acquired in step S330. The geodesic distance from the nipple may be obtained, on the surface model. These methods are advantageous in that a value closer to the actual geodesic distance than the direct distance from the nipple to the body surface point can be obtained.

Modified Example 2

In the present exemplary embodiment, the following method has been described as an example. Specifically, the candidates of the corresponding point are narrowed down based on the ratio between the direct distance $f_j$ and the geodesic distance $g_k$ in the operation in step S3620. The corresponding point is selected from the candidates of the corresponding point based on the direct distance $f_j$. However, this is not the only method available.

For example, as a first method, the following processing may be performed on each body surface point $q_j$ of the subject in the supine posture. Three dimensional distances between the body surface point $q_j$ of the subject in the supine posture and the positional coordinates of the $r_k(c)$ of the vertices $p_k$ of all the meshes may be obtained. A value obtained by weighting the three dimensional distance in accordance with the difference between the geodesic distance $g_k$ and the direct distance $f_j$ is set as an evaluation value of for the matching. The vertex $p_k$ of the mesh with the smallest evaluation value may be set as the corresponding point of the body surface point $q_j$ of the subject in the supine posture.

The following method may be used as a second method. For example, a difference (three dimensional vectors) between the position coordinate $r_k(c)$ of the vertex $p_k$ of the mesh after the deformation and the position coordinate $t_j$ of the body surface point $q_j$ of the subject in the supine posture is calculated. Then, a four dimensional vector is generated by coupling to the three dimensional vector a differential value (scalar value) between the geodesic distance $g_k$ in the prone posture and the direct distance $f_j$ in the supine posture related to the body surface point. A norm (Euclidean norm) of the four dimensional vector may be calculated and used as the evaluation value for the matching.

The second modification described above is different from the method described in the present exemplary embodiment in that the candidates of the corresponding point need not to be narrowed down, and thus is advantageous in that the processing can be performed through a simpler procedure.

Modified Example 3

In the present exemplary embodiment, an example has been described where the deformation model is generated in the operation in step S320, and the deformation parameter is calculated in the operation in step S360. However, this is not the only procedure available.

For example, the vertex group of the meshes indicated by the simulation results $d_i$ obtained in step S310 may be compared with the body surface point group of the subject in the supine posture. In this case, the simulation result with the closest shape may be searched for, and the deformed MRI image may be generated based on the result.

Specifically, the body surface point group $q_j$ of the subject in the supine posture, acquired in step S330, performs a translational motion so that the nipple of the subject in the supine posture is positioned at the origin. Then, for each of the simulation results $d_i$, matching the position coordinates $d_{ki}$ of the vertices $p_k$ of the meshes after the deformation with the body surface point group $q_j$ of the subject in the supine posture is performed. The sum of the three dimensional distances between the matching points is set as the evaluation value. As in step S3620, the candidates of the corresponding point can be narrowed down based on the relationship between the geodesic distance $g_k$ from the nipple to the body surface point $q_j$ of the subject in the supine posture, and the direct distance $f_j$ from the nipple to the body surface point $q_j$ of the subject in the supine posture. The simulation result $d_i$ with the smallest evaluation value is used as the shape closest to the body surface shape of the subject in the supine posture.

Next, a second exemplary embodiment of the present invention will be described. The basic principle of the first exemplary embodiment is that the direct distance $f_j$ from the nipple to the surface point of the subject in the supine posture is calculated for each surface point $q_j$. The present exemplary embodiment is different from the first exemplary embodiment in that information on the dense body surface of the subject in the supine posture is obtained. The geodesic distance from the nipple to the body surface point is calculated as the second distance from the information. The candidates of the corresponding point are narrowed down by using the geodesic distance thus calculated. Owing to a characteristic that the geodesic distance from the nipple to the body surface point does not largely change in accordance with the position, the body surface point of the subject in the supine posture can be more accurately matched with the vertex of the mesh (body surface point of the subject in the prone posture). Thus, the calculated deformation parameter more accurately represents the shape of the breast of the subject in the supine posture. As described above, the present exemplary embodiment is different from the first exemplary embodiment mainly in the method for calculating the distance from the nipple to the body surface point $q_j$ of the subject in the supine posture. In the description of the present exemplary embodiment, the portions same as the counterparts in the first exemplary embodiment is provided with the same reference numerals in FIGS. 1 to 4, and will not be described in detail.

Figure 5:
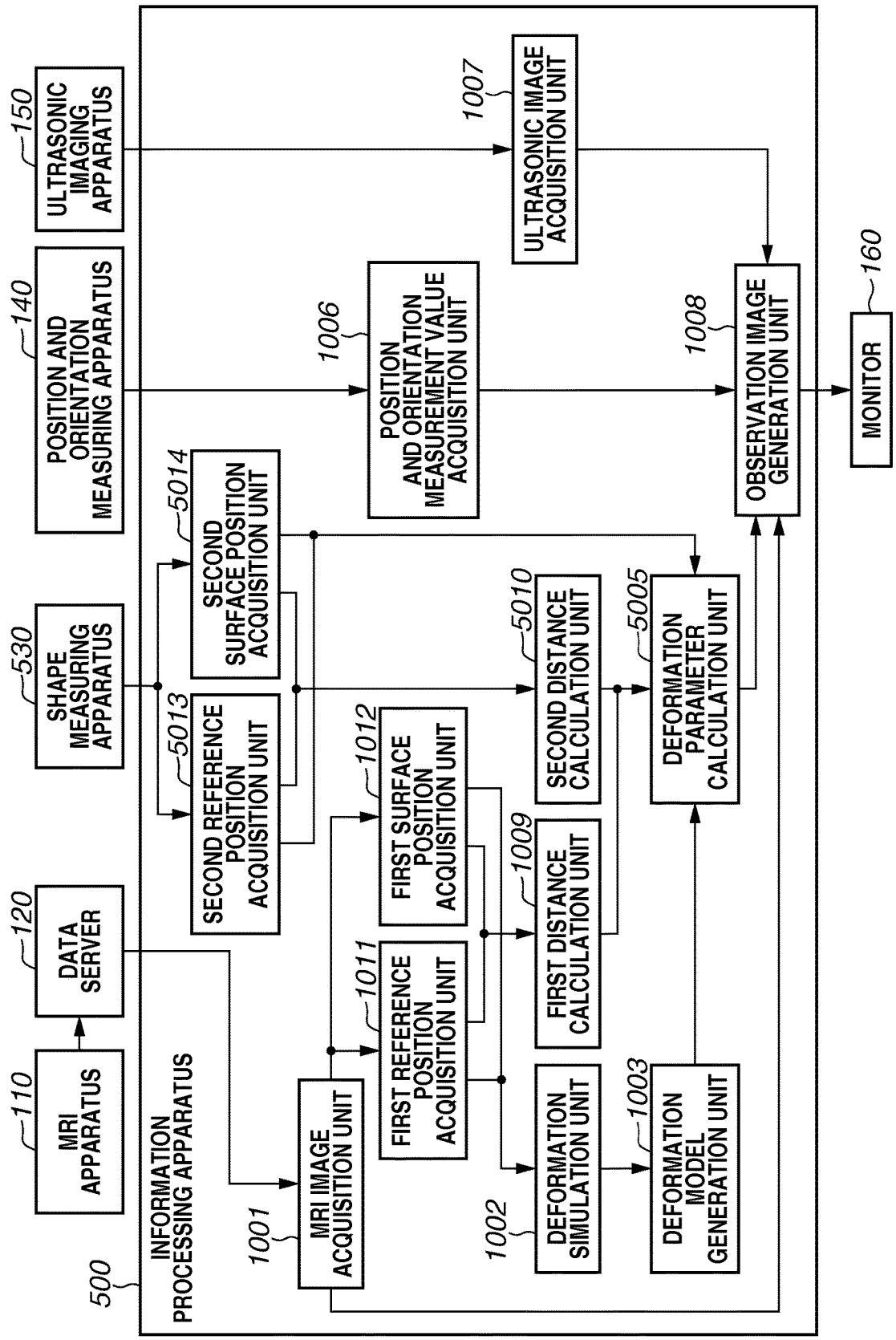
FIG. 5 is a diagram illustrating a second example of the configuration of the diagnostic system.

FIG. 5 is a diagram illustrating an example of a configuration of a diagnostic system of the present exemplary embodiment.

A shape measuring apparatus 530 is an apparatus that measures a body surface shape of the subject. The shape measuring apparatus 530 is formed of conventionally known members such as a range sensor that optically measures the shape of the subject in a contactless manner, for example.

A second distance calculation unit 5013 performs third acquisition processing of detecting the nipple position from shape data of the subject at the time of ultrasonography to acquire the nipple position as a second reference position. The shape data of the subject is measured by the shape measuring apparatus 530

A second surface position acquisition unit 5014 performs fourth acquisition processing of extracting an area corresponding to the body surface of the breast from the shape data of the subject at the time of ultrasonography, and acquiring the positions of several body surface points in the extracted area as second surface positions. The shape data of the subject is measured by the shape measuring apparatus 530.

A second distance calculation unit 5010 performs second calculation processing of calculating the geodesic distance from the nipple to each body surface point of the subject in the supine posture, based on the nipple position acquired by the second distance calculation unit 5013 and the body surface shape of the subject in the supine posture acquired by the second surface position acquisition unit 5014. A deformation parameter calculation unit 5005 acquires the deformation model generated by the deformation model generation unit 1003. Further, the deformation parameter calculation unit 5005 acquires the geodesic distance from the nipple to the body surface point in the prone posture calculated by the first distance calculation unit 1009. The deformation parameter calculation unit 5005 further acquires the geodesic distance from the nipple to the body surface point in the supine posture calculated by the second distance calculation unit 5010. The deformation parameter calculation unit 5005 performs matching of the body surface point in the prone posture and the body surface point in the supine posture, based on the deformation model, the geodesic distance from the nipple to the body surface in the prone posture, and the geodesic distance from the nipple to the body surface in the supine posture. The deformation parameter calculation unit 5005 calculates the parameter vector of the deformation model based on the result of the matching.

Figure 6:
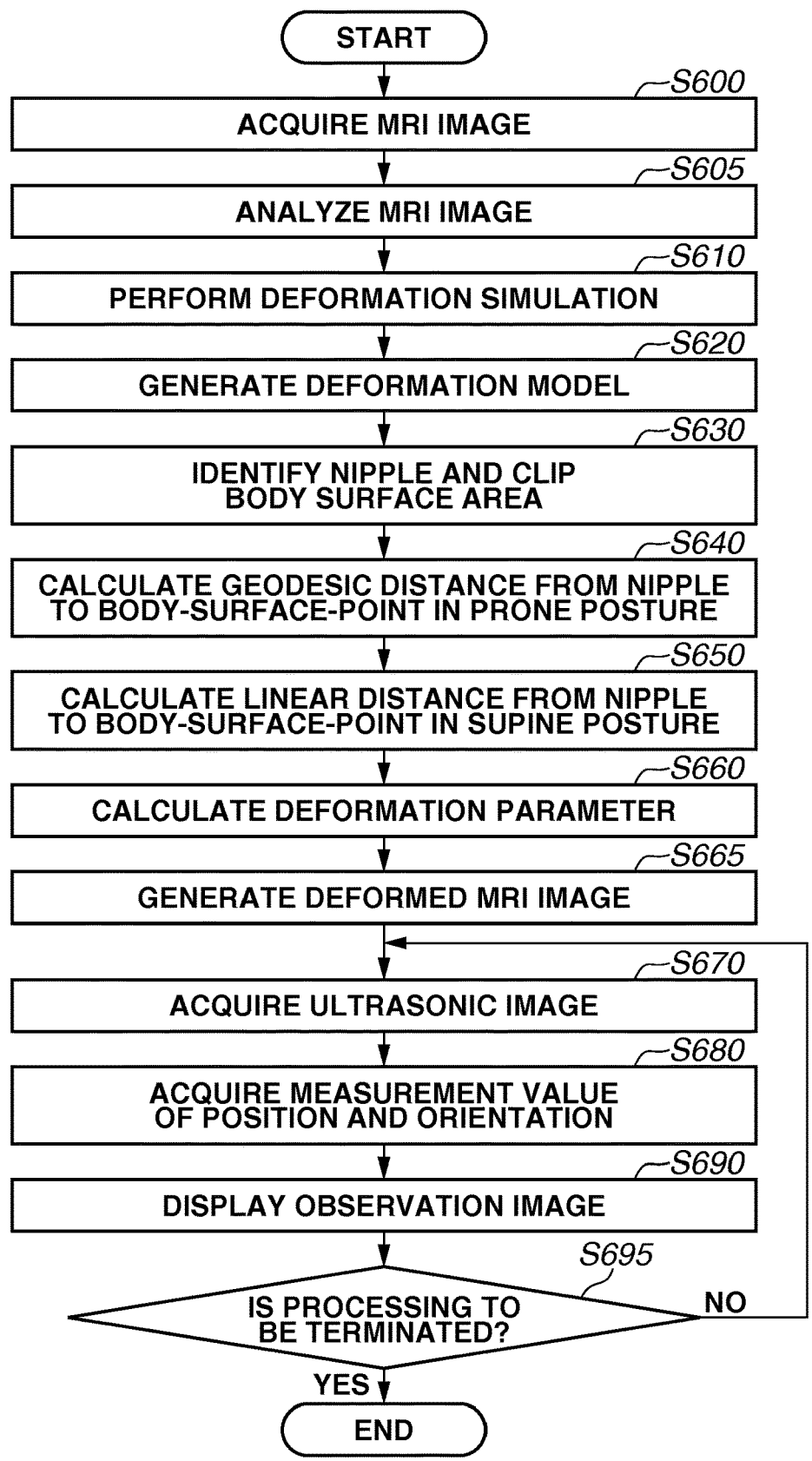
FIG. 6 is a flowchart illustrating a second example of the entire processing performed by the information processing apparatus.

An example of the entire operation performed by the information processing apparatus 500 is described in detail by referring to a flowchart in FIG. 6. The operations in steps S600 to S620, S640, and S665 to S695 are respectively the same as the operations in S300 to S320, S340, and S365 to S395 in FIG. 3 and thus will not be described in detail.
(Step S630)

In step S630, the second distance calculation unit 5013 detects a protrusion in the shape data measured by the shape measuring apparatus 530 to identify the nipple and acquire the nipple position. The second surface position acquisition unit 5014 performs processing of clipping an area corresponding to the body surface of the breast from the shape data measured by the shape measuring apparatus 530.
(Step S650)

In step S650, the second distance calculation unit 5010 calculates the geodesic distance from the nipple to each of the body surface points $q_j$ ($1 \le j \le L$) of the subject in the supine posture from the measurement values of the body surface shape of the subject acquired in step S630.
(Step S660)

In step S660, the deformation parameter calculation unit 5005 calculates the deformation parameter of the deformation model in such a manner that the deformation state represented by the deformation model generated in step S620 substantially matches the measurement values of the body surface points of the subject in the supine posture acquired in step S630. The operation in this step S660 is generally the same as the operation performed by the deformation parameter calculation unit 1005 in step S360.

Still the operation in S660 is different from the operation in step S360 in that the candidates of the corresponding points of the vertexes $p_k$ of the meshes and the body surface points $q_j$ of the subject in the supine posture are narrowed down based on the relationship between the geodesic distances from the nipple (for example, whether the ratio between the geodesic distances is within the predetermined range). In the first exemplary embodiment, the matching between each body surface point $q_j$ ($1 \le j \le L$) of the subject in the supine posture, and the vertex $p_k$ of the mesh is performed in step S3620. In contrast, according to the present exemplary embodiment, matching each of the vertices $p_k$ ($1 \le k \le Q$) of the meshes and the body surface point $q_j$ of the subject in the supine posture is performed.

In the first exemplary embodiment, in step S3630, the deformation of the subject with the minimum sum of the distances between all the body surface points $q_j$ of the subject in the supine posture and the corresponding points is estimated in step S3630. In the present exemplary embodiment, the deformation of the subject with the minimum sum of the distances between all the vertices $p_k$ of the meshes and the corresponding points is estimated.

The operation by an information processing apparatus 500 is performed as described above.

As described above, in the present exemplary embodiment, the matching between the body surface point $q_j$ of the subject of in the supine posture, and the vertex $p_k$ of the mesh can be accurately performed based on the characteristic that the geodesic distance from the nipple to each body surface point does not largely change in accordance with the position.

As a result, the deformation of the observation portion such as the breast caused by the change in the body posture of the subject can be more accurately estimated.

The modifications described in the first exemplary embodiment can also be applied in the present exemplary embodiment.

Next, a third exemplary embodiment of the present invention will be described. In the first exemplary embodiment, the deformation of the shape of the subject (the breast of the subject) occurring when the subject changes to the supine posture is calculated through the simulation, and the deformation model is calculated through the deformation. The matching of the body surface point in the prone posture and the body surface point in the spine posture is performed based on the deformation model, the geodesic distance from the nipple to the body surface in the prone posture, and the direct distance from the nipple to the body surface in the supine posture. In the present exemplary embodiment, a statistical model related to the shape and the deformation of the breast is calculated. The matching of the body surface point in the prone posture and the body surface point in the spine posture is performed based on the statistical model, the geodesic distance from the nipple to the body surface in the prone posture, and the direct distance from the nipple to the body surface in the supine posture. As described above, the present exemplary embodiment is mainly different from the first exemplary embodiment in part of the processing for matching the body surface point in the prone posture and the body surface point in the supine posture. Thus, in the present exemplar embodiment, the portions that are same as the counterparts in the first exemplary embodiment are provided with the reference numerals in FIGS. 1 to 4 and will not be described in detail.

In the present exemplary embodiment, a matching relation between the MRI image of the subject in the supine posture and the ultrasonic image of the subject in the supine posture is clarified in the same manner as the first exemplary embodiment. Specifically, the present exemplary embodiment uses the body surface shape in each of the prone posture and the supine posture and the geodesic distance and the direct distance from the nipple to the body surface. The matching is displayed so as to be visually recognizable by the user.

Figure 7:
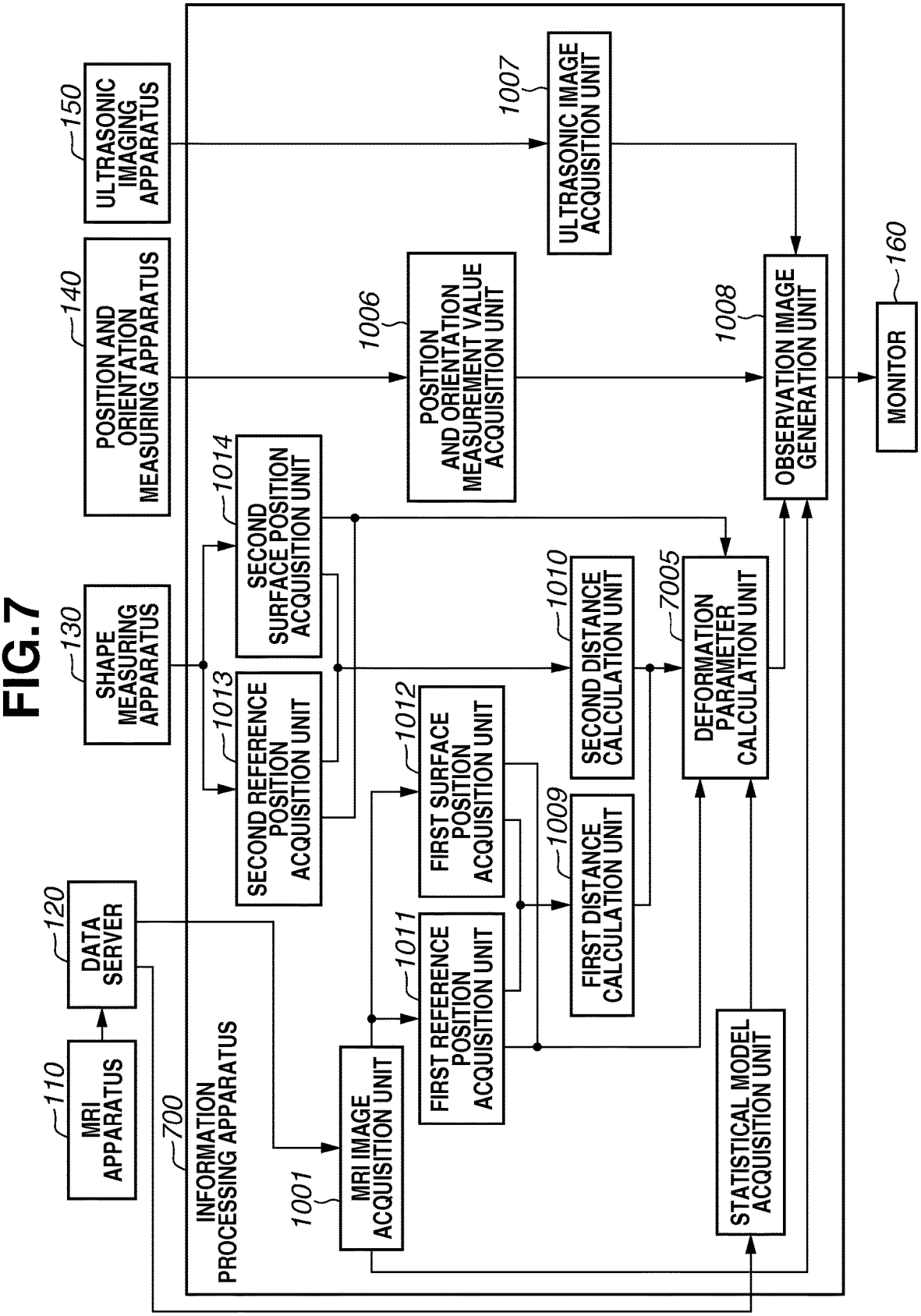
FIG. 7 is a diagram illustrating a third example of the configuration of the diagnostic system.

FIG. 7 is a diagram illustrating an example of a configuration of a diagnostic system of the present exemplary embodiment. The diagnostic system of the present exemplary embodiment is different from the diagnostic system of the first exemplary embodiment illustrated in FIG. 1 in that a statistical model acquisition 7015 is provided instead of the deformation simulation unit 1002 and the deformation model generation unit 1003. The operation performed by the deformation parameter calculation unit 7005 is different from that performed by the deformation parameter calculation unit 1005 in the first exemplary embodiment. The operations performed by the other components are the same as the counterparts in the first exemplary embodiment.

The statistical model acquisition unit 7015 acquires a statistical model related to the shape and the deformation of the breast from the data server 120. The statistical model is generated based on a number of deformation sample data pieces of the shape of the breast in the prone posture and the supine posture. A specific example of the statistical model is described in detail along with the operations in the present exemplary embodiment.

The deformation parameter calculation unit 7005 acquires the statistical model acquired by the statistical model acquisition unit 7015. The deformation parameter calculation unit 7005 acquires the geodesic distance from the nipple to the body surface in the prone posture calculated by the first distance calculation unit 1009. The deformation parameter calculation unit 7005 acquires the direct distance from the nipple to the body surface calculated by the second distance calculation unit 1010. The deformation parameter calculation unit 7005 calculates the deformation parameter based on the statistical model, the geodesic distance from the nipple to the body surface in the prone posture, and the direct distance from the nipple to the body surface. The deformation parameter is used to approximate the deformation of the subject breast caused by the change from the prone posture to the supine posture using the statistical model.

Figure 8:
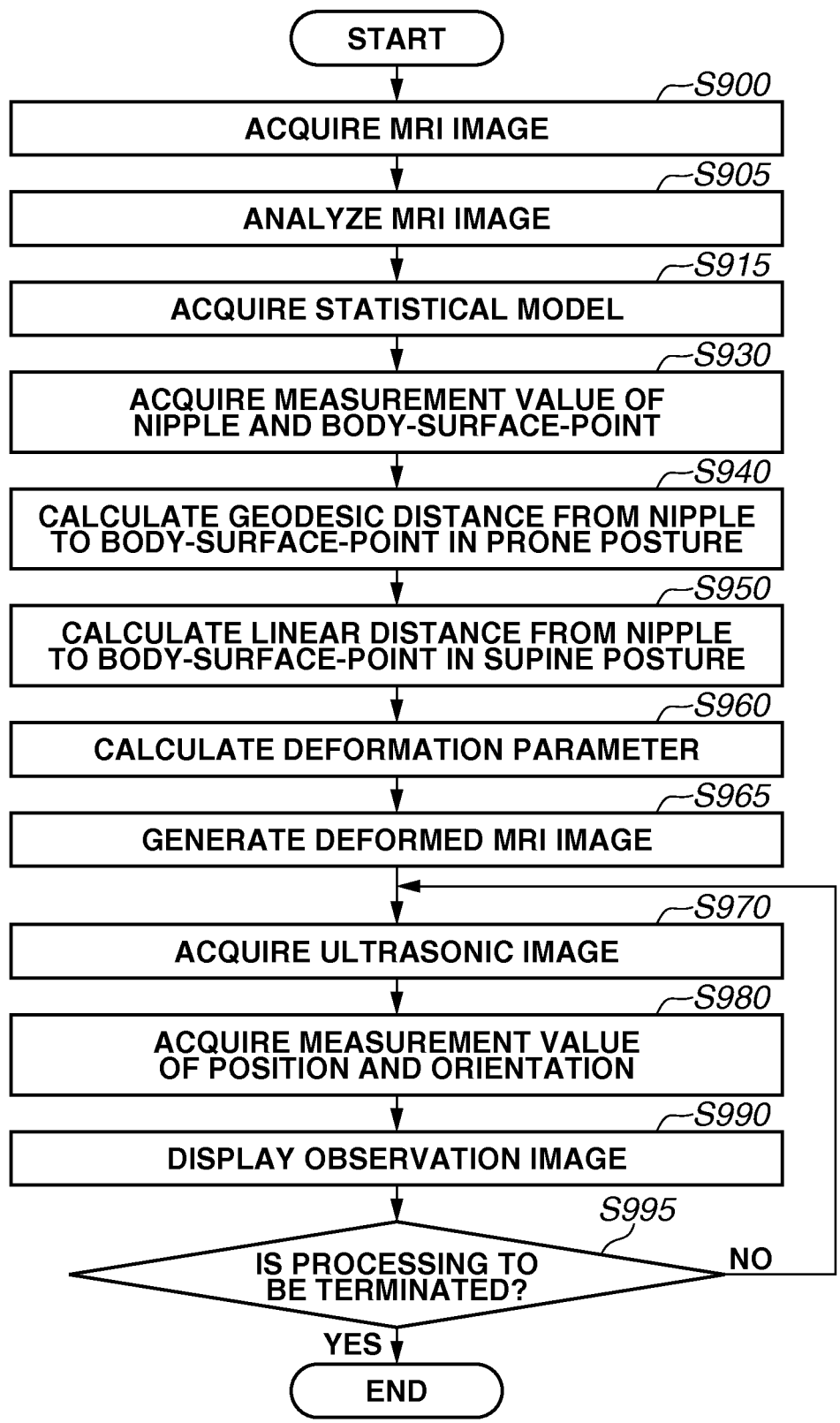
FIG. 8 is a flowchart illustrating a third example of the entire processing performed by the information processing apparatus.

Next, an example of the entire processing performed by an information processing apparatus 700 will be described in detail by referring to a flowchart in FIG. 8. The operations in steps S900, S905, S930 to S950, and S965 to S995 are respectively the same as the operations in S300, S305, S330 to S350, and S365 to S395 in FIG. 3, and thus will not be described in detail.

(Step S915)

In step S915, the statistical model acquisition unit 7015 acquires the statistical model related to the shape and the deformation of the breast, accumulated in the data server 120. In the present exemplary embodiment, the statistical model generated by the following method is stored in the data server 120 in advance.

In the present example, the statistical model is generated by statistical processing of behavior of the shape and the deformation in a plurality of sample data pieces. MRI images of a single breast captured in two different types of positions (the prone posture and the supine posture) is used here as a single sample data piece. More specifically, the statistical model is generated based on data in which arbitrary image coordinate value in a first MRI image of the breast of the subject in the prone posture is matched with an image coordinate value in a second MRI image of the portion that is the same as that in the first MRI image in the supine posture. The data serves as a correct value of the deformation.

A method of obtaining the statistical model is described in detail. Meshes are set in MRI images of the breast of the subject in the prone posture of each case, in such a manner that, anatomically, the same node is positioned at substantially the same positions between the samples. Next, the position of the node of the mesh in the supine posture is calculated based on the correct value of the deformation in each case. A vector obtained by lining up the coordinates of the position of the nodes of the meshes in the prone posture and the supine posture in samples is defined as a sample vector $x_{sample,i}$. The statistical model is obtained by statistically analyzing the sample vector group thus generated. The sample vector group can be statistically analyzed by principal component analysis, for example. In this case, an average vector $x_{average}$ and principal component vectors $e_d$ ($1 \leq d \leq M$) of the sample group are calculated. In the present exemplary embodiment, the vectors are referred to as the statistical model, and thus the statistical model is obtained by calculating the vectors, and "M" is the number of principal components calculated by the principal component analysis.

The statistical model is further described. The statistical model obtained in the present exemplary embodiment serves as a statistical description of the deformation as a relationship between the shapes of the breast in the prone and the supine postures in the sample data. For example, sets of shapes before and after various deformations including the sample vector $x_{sample,i}$ can be generated by calculating linear sum obtained by weighting the average vector $x_{average}$ and the principle vector $e_d$ with the parameters $c_1$ to $c_M$ as expressed in the following formula (8).

$$x \cong x_{average} + \sum_{d=1}^{D} c_d e_d \qquad (8)$$

The formula (8) can be rewritten in a matrix and vector format, as expressed with the following formula (9).

$$x \cong x_{average} + Ec \qquad (9)$$

In the above-described formula (9), "E" is a matrix including the arranged principal component vectors $e_d$, and is referred to as a principal component matrix, and "c" represents a vector including the arranged coefficients $c_d$, and is referred to as a coefficient vector. The statistical model acquired in the present exemplary embodiment can express various shapes and deformations of the breast which include the sample data, by changing the coefficient vector c in various manners.

(Step S960)

Figure 9:
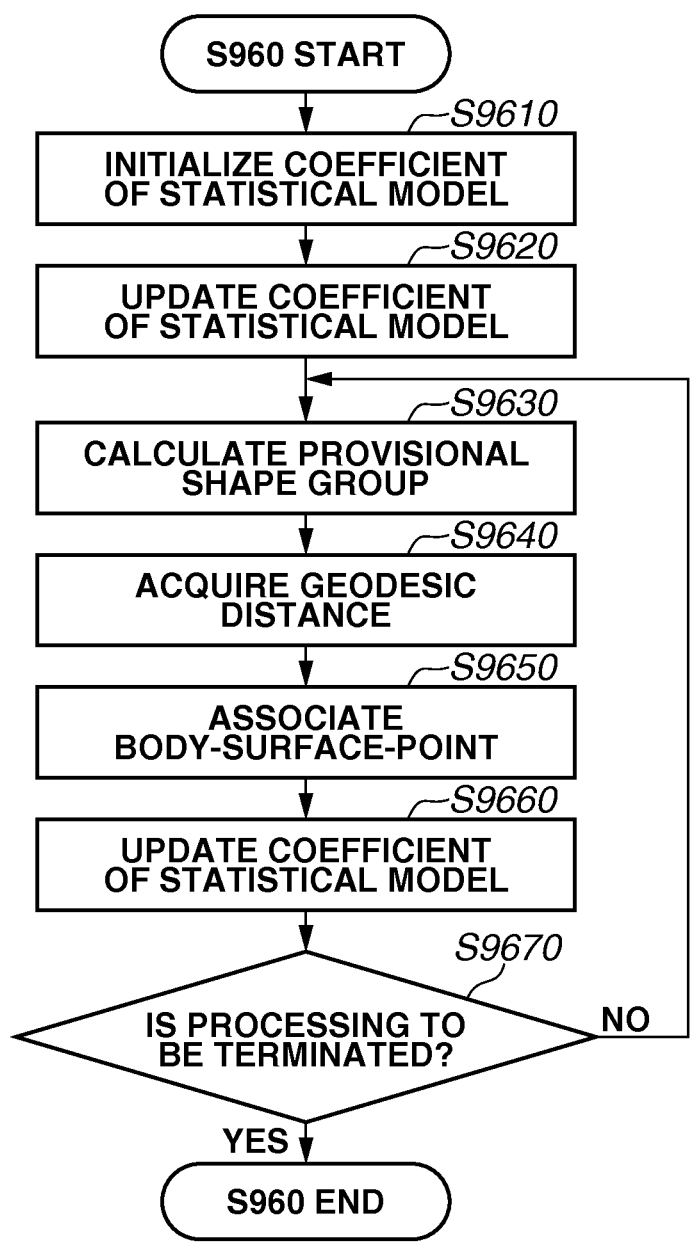
FIG. 9 is a flowchart illustrating an operation in step S960 in detail.

In step S960, the deformation parameter calculation unit 7005 calculates a coefficient of the statistical model and a stiffness conversion as the deformation parameter. The coefficient of the statistical model and the stiffness conversion are calculated based on the body surface points (the shape defined by the body surface points) of the subject in the prone posture and the nipple position acquired in step S905, and the body surface points (the shape defined by the body surface points) of the subject in the supine posture and the nipple posture acquired in step S930. An example of the operation step S960 is described below in detail by referring to a flowchart in FIG. 9.

(Step S9610)

In step S9610, the deformation parameter calculation unit 7005 sets an initial value c of the coefficient to the statistical model. The initial value c' may be a zero vector for example.

(Step S9620)

In step S9620, the deformation parameter calculation unit 7005 generates candidates $c''_h$ ($1 \leq h \leq H_1$) of the coefficient of the statistical model based on a provisional value c' of the coefficient of the statistical model. The deformation parameter calculation unit 7005 calculates shapes $x''_h$ from the respective candidates $c''_h$ of the coefficient of the statistical model thus generated through the calculation formula (9). The deformation parameter calculation unit 7005 uses a conventionally known method such as an iterative closest point (ICP) algorithm to obtain the level of matching of the shapes $x''_h$ and the body surface shape of the subject in the supine posture acquired in step S930. The deformation parameter calculation unit 7005 selects the coefficient $c''_h$ that gives the shape $x''_h$ that is most likely to match the body surface shape of the subject in the supine posture, as the new provisional coefficient value c'. The deformation parameter calculation unit 7005 sets the shape determined by the new provisional coefficient value c' as the new provisional shape x'. The operations (generating $c''_h$ and updating c') are repeatedly performed until a predetermined termination condition is satisfied.

(Step S9630)

In step S9630, the deformation parameter calculation unit 7005 generates the candidates $c''_h$ ($1 \leq h \leq H_2$) of the coefficient of the statistical model through a method that is the same as that in step S9620, based on the provisional value c' of the coefficient. The deformation parameter calculation unit 7005 calculates a provisional shape group $x''_h$ based on the candidates of the coefficient of the statistical model.

(Step S9640)

In step S9640, the deformation parameter calculation unit 7005 acquires the geodesic distance from the nipple which is in the state before the deformation, for each of a body surface node (vertex of the mesh) of the provisional shape $x''_h$ before the deformation. The operation can be performed through a method that is the same as that in step S3615 in the first exemplary embodiment. The operation described above is performed on each of the provisional shapes $x''_h$.

(Step S9650)

In step S9650, the deformation parameter calculation unit 7005 performs matching of each body surface point $q_j$ ($1 \leq j \leq L$) of the subject in the supine posture and the body surface nodes of the provisional shape $x''_h$ before and after the deformation. At this time, the deformation parameter calculation unit 7005 compares the geodesic distance (acquired in step S9640) from the nipple to each body surface node of the provisional shape $x''_h$ before deformation, and the direct distance (calculated in step S950) from the nipple to the body surface point $q_j$ of the subject in the supine posture. The deformation parameter calculation unit 7005 narrows down the candidates of the corresponding point based on the relationship between the distances. The method that is the same as that in step S3620 in the first exemplary embodiment can be used to narrow down the candidates of the corresponding point. The deformation parameter calculation unit 7005 selects from among the candidates of the corresponding point a point where the body surface node after the deformation is positioned closest to the body surface point $q_j$ of the subject in the supine posture, as the corresponding point. The operation described above is performed on each of the provisional shape group $x''_h$.

(Step S9660)

In step S9660, the deformation parameter calculation unit 7005 selects the shape which shows a minimum average value of the distances between the corresponding points obtained in step S9650, from the provisional shape group $x''_h$. The variable candidate $c''_h$ of the coefficient from which the shape is obtained is set as the new provisional value c' of the coefficient of the statistical model.

(Step S9670)

In step S9670, the deformation parameter calculation unit 7005 determines whether to terminate the processing in step S960. The processing is terminated when a predetermined condition is satisfied. When the predetermined condition is not satisfied, the operations at and after step S9630 are repeated using a new provisional value of the coefficient c' of the statistical model.

The deformation estimation operation in step S960 is performed as described above.

The processing by the information processing apparatus 700 is performed as described above.

As described above, in the present exemplary embodiment, the MRI image of the subject in the probe position in a target case can be deformed into a shape of a breast in the supine posture estimated by using the sample data. Thus, the MRI image of the breast of the subject in the prone posture deformed to be easily compared with the ultrasonic image can be presented. In the present exemplary embodiment, the erroneous matching can be prevented even when a body surface node that is actually not the corresponding point is positioned close to the body surface point $q_j$ of the subject in the supine posture, as in the first exemplary embodiment. As a result, the deformation of the observation portion such as the breast caused when the subject changes the body posture can be more accurately estimated.

The modifications described in the first exemplary embodiment can also be applied in the present exemplary embodiment. The method of the present exemplary embodiment can be applied to the second exemplary embodiment.

Figure 10:
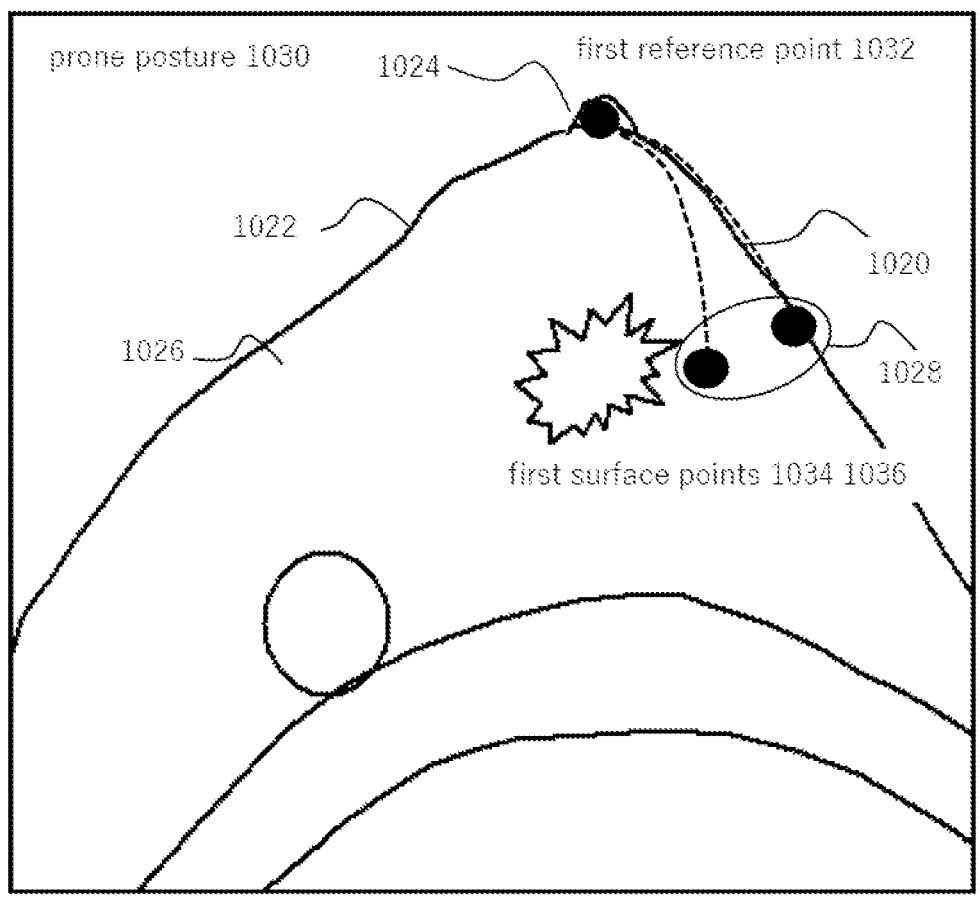
FIG. 10 illustrates geodesic distance in a prone posture for a breast image.
Figure 11:
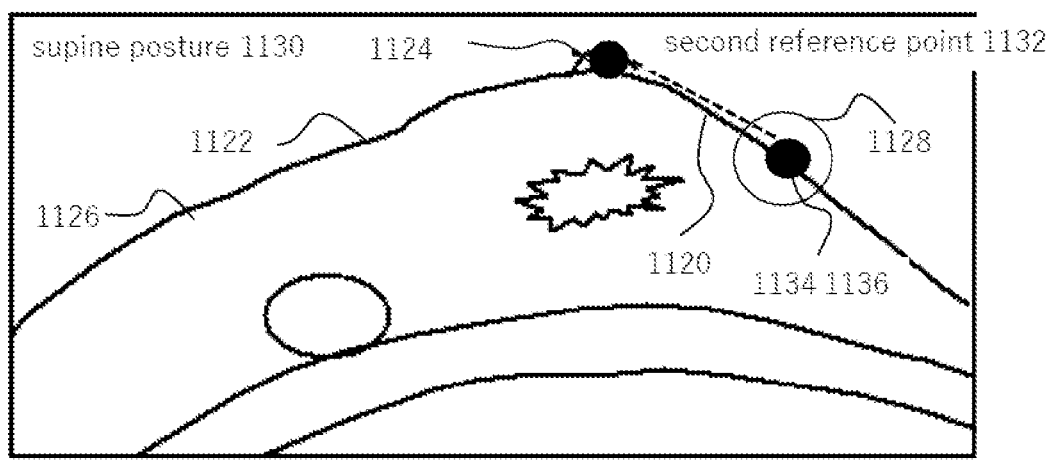
FIG. 11 illustrates Euclidian distance in a supine posture for a breast image.

FIG. 10 illustrates geodesic distance in a prone posture for a breast image. FIG. 11 illustrates Euclidian distance in a supine posture for a breast image. In an example as in FIG. 10, the information processing apparatus 100 calculates a geodesic distance 1020 (shortest distance measured along the body surface 1022) from the nipple 1024 of the breast 1026 in the FIG. 10 breast image to the body surface point group 1028 in the case of the prone posture 1030. The first reference position acquisition unit 1011 acquires the nipple position 1032 as a first reference position (first reference point 1032) as illustrated in FIG. 10 on the breast surface 1022 in the prone posture 1030. The first surface position acquisition unit 1012 acquires a body posture 1034 of a first surface point 1036 on the breast surface 1022 in the prone posture 1030. In an example as in FIG. 11, the information processing apparatus 100 calculates the Euclidian distance 1120 measured along the body surface 1122, from the nipple 1124 of the breast 1126 in the FIG. 11 breast image to the body surface point group 1128 in the case of the supine posture 1130. The second reference position acquisition unit 1013 acquires the nipple position 1132 at the time of ultrasonography measured by the shape measuring apparatus 130, as a second reference position (second reference point 1132) as illustrated in FIG. 11 on the breast surface 1122 in the prone posture 1130, which is different from the prone posture 1030. The second surface position acquisition unit 1014 acquires a position 1134 of a second surface point 1136 as a point on the breast surface 1122 in the supine posture 1130.

The exemplary embodiments described above are merely specific examples for implementing the present invention, and thus should not be interpreted as limiting the technical scope of the present invention. The present invention can be implemented in various forms without departing from the technical idea or a main feature of the present invention.

Other Embodiments

The present invention is implemented by the following processing. Software (a computer program) for implementing functions of the exemplary embodiment described above is supplied to a system or an apparatus through a network or various storage media. A computer (or a CPU, a microprocessor unit (MPU), or the like) of the system of the apparatus reads out and executes the program.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-003647 filed Jan. 10, 2014, which is hereby incorporated by reference herein in its entirety.

What is claimed is:

1. An information processing apparatus comprising:
one or more processors; and
memory storing instructions that, when executed by the one or more processors, cause the information processing apparatus to perform operations including:
acquiring, as a first acquiring, a position of a first reference point as a reference point on a surface of a target object in a first body posture,
acquiring, as a second acquiring, positions of a plurality of first surface points different from the first reference point as a plurality of points on the surface of the target object in the first body posture,
acquiring, as a third acquiring, a position of a second reference point as a reference point on the surface of the target object in a second body posture, wherein the second body posture is different from the first body posture,
acquiring, as a fourth acquiring, a position of a second surface point different from the second reference point as a point on the surface of the target object in the second body posture,
calculating, as a first calculation, a plurality of first distances between the position of the first reference point and the positions of the plurality of first surface points,
calculating, as a second calculation, a second distance between the position of the second reference point and the position of the second surface point, and
selecting, from the plurality of first surface points, one point that corresponds to the second surface point based on a relationship of (i) the plurality of first distances between the position of the first reference point and the positions of the plurality of first surface points and (ii) the second distance between the position of the second reference point and the position of the second surface point,
wherein each of the plurality of first distances is a geodesic distance between the position of the first reference point and each of the positions of the plurality of first surface points, and
wherein the second distance is a Euclidian distance between the position of the second reference point and the position of the second surface point.

2. The information processing apparatus according to claim 1,
wherein the first acquiring acquires the position of the first reference point based on a result of analysis on an image obtained by capturing an image of the target object in the first body posture,
wherein the second acquiring acquires the positions of the plurality of first surface points based on the result of the analysis on the image obtained by capturing the image of the target object in the first body posture,
wherein executing the instructions further causes the information processing apparatus to perform operations including:
narrowing down candidates of a first surface point and the second surface point that corresponds to each other in the plurality of first surface points and a plurality of second surface points, based on a relationship between the plurality of first distances and a plurality of second distances, wherein the plurality of second distances is between the position of the second reference point and positions of the plurality of second surface points, and
estimating positions of a plurality of points matching the plurality of first surface points in a case where processing of deforming the image obtained by capturing the image of the target object in the first body posture is performed in such a manner that the first body posture is changed to the second body posture, and
wherein selecting includes selecting, from the narrowed down candidates and the estimated positions of the plurality of points matching the plurality of first surface points, a point closest to the position of the second surface point in the second body posture and the second surface point in the second body posture.

3. The information processing apparatus according to claim 2, wherein narrowing down includes setting, as the candidates of the first surface point and the second surface point that corresponds to each other, points showing a ratio between a first distance and the second distance or a difference between the first distance and the second distance, within a range between a lower limit value and an upper limit value, from the plurality of first surface points and the plurality of second surface points.

4. The information processing apparatus according to claim 3, wherein narrowing down includes changing at least one of the lower limit value and the upper limit value in accordance with the first distance or the second distance.

5. The information processing apparatus according to claim 1,
wherein the first acquiring acquires the position of the first reference point based on a result of analysis on an image obtained by capturing an image of the target object in the first body posture,
wherein the second acquiring acquires positions of the plurality of first surface points, based on the result of the analysis on the image obtained by capturing the image of the target object in the first body posture, wherein executing the instructions further causes the information processing apparatus to perform operations including estimating positions of a plurality of points matching the plurality of first surface points in a case where processing of deforming the image obtained by capturing the image of the target object in the first body posture is performed in such a manner that the first body posture is changed to the second body posture, wherein selecting includes selecting one point from the plurality of first surface points and one point from a plurality of second surface points that match with each other, based on the estimated positions of the plurality of points matching the plurality of first surface points, positions of the plurality of second surface points in the second body posture, and a relationship between the plurality of first distances and a plurality of second distances, and wherein the plurality of second distances is between the position of the second reference point and the positions of the plurality of second surface points.

6. The information processing apparatus according to claim 1, wherein the third acquiring acquires the position of the second reference point based on a result of measurement performed by a measurement apparatus configured to measure a shape of the target object, and wherein the fourth acquiring acquires positions of a plurality of second surface points based on the result of the measurement performed by the measurement apparatus.

7. A method for an information processing apparatus, the method comprising:

acquiring, as a first acquiring, a position of a first reference point as a reference point on a surface of a target object in a first body posture;

acquiring, as a second acquiring, positions of a plurality of first surface points different from the first reference point as a plurality of points on the surface of the target object in the first body posture;

acquiring, as a third acquiring, a position of a second reference point as a reference point on the surface of the target object in a second body posture, wherein the second body posture is different from the first body posture;

acquiring, as a fourth acquiring, a position of a second surface point different from the second reference point as a point on the surface of the target object in the second body posture;

calculating, as a first calculation, a plurality of first distances between the position of the first reference point and the positions of the plurality of first surface points;

calculating, as a second calculation, a second distance between the position of the second reference point and the position of the second surface point; and selecting, from the plurality of first surface points, one point that corresponds to the second surface point based on a relationship of (i) the plurality of first distances between the position of the first reference point and the positions of the plurality of first surface points and (ii) the second distance between the position of the second reference point and the position of the second surface point, wherein each of the plurality of first distances is a geodesic distance between the position of the first reference point and each of the positions of the plurality of first surface points, and wherein the second distance is a Euclidian distance between the position of the second reference point and the position of the second surface point.

8. A non-transitory computer-readable storage medium storing a program to cause a computer to perform a method for an information processing apparatus, the method comprising:

acquiring, as a first acquiring, a position of a first reference point as a reference point on a surface of a target object in a first body posture;

acquiring, as a second acquiring, positions of a plurality of first surface points different from the first reference point as a plurality of points on the surface of the target object in the first body posture;

acquiring, as a third acquiring, a position of a second reference point as a reference point on the surface of the target object in a second body posture, wherein the second body posture is different from the first body posture;

acquiring, as a fourth acquiring, a position of a second surface point different from the second reference point as a point on the surface of the target object in the second body posture;

calculating, as a first calculation, a plurality of first distances between the position of the first reference point and the positions of the plurality of first surface points;

calculating, as a second calculation, a second distance between the position of the second reference point and the position of the second surface point; and selecting, from the plurality of first surface points, one point that corresponds to the second surface point based on a relationship of (i) the plurality of first distances between the position of the first reference point and the positions of the plurality of first surface points and (ii) the second distance between the position of the second reference point and the position of the second surface point, wherein each of the plurality of first distances is a geodesic distance between the position of the first reference point and each of the positions of the plurality of first surface points, and wherein the second distance is a Euclidian distance between the position of the second reference point and the position of the second surface point.

9. The information processing apparatus according to claim 1, wherein the first acquiring acquires the position of the first reference point based on a magnetic resonance imaging (MRI) image obtained by capturing an image of the target object in a prone posture as the first body posture, wherein the second acquiring acquires the positions of the plurality of first surface points based on the MRI image, wherein the third acquiring acquires the position of the second reference point based on an ultrasonic image obtained by capturing an image of the target object in a supine posture as the second body posture, and wherein the fourth acquiring acquires the position of the second surface point based on the ultrasonic image.

10. The information processing apparatus according to claim 1, wherein the first acquiring acquires the position of the first reference point based on a result of analysis on an image obtained by capturing an image of the target object in the first body posture, and wherein the second acquiring acquires the positions of the plurality of first surface points based on the result of the analysis on the image obtained by capturing the image of the target object in the first body posture.

11. The information processing apparatus according to claim 1,
wherein executing the instructions further causes the information processing apparatus to perform operations including estimating a position of a point matching a first surface point in a case where processing of deforming an image obtained by capturing an image of the target object in the first body posture is performed in such a manner that the first body posture is changed to the second body posture,
wherein selecting includes selecting one point from the plurality of first surface points and one point from a plurality of second surface points that match with each other, based on the estimated position of the point matching the first surface point, positions of the plurality of second surface points in the second body posture, and a relationship between the plurality of first distances and a plurality of second distances, and
wherein the plurality of second distances is between the position of the second reference point and the positions of the plurality of second surface points.

* * * * *